US005884230A

United States Patent [19]
Srinivasan et al.

[11] Patent Number: 5,884,230
[45] Date of Patent: Mar. 16, 1999

[54] METHOD AND SYSTEM FOR PROTEIN MODELING

[75] Inventors: Subhashini Srinivasan, Kirkland; Padmanaban Sudarsanam, Kent, both of Wash.

[73] Assignee: Immunex Corporation, Seattle, Wash.

[21] Appl. No.: 663,809

[22] Filed: Jun. 14, 1996

Related U.S. Application Data

[63] Continuation-in-part of Ser. No. 55,050, Apr. 28, 1993, Pat. No. 5,453,937, and a continuation-in-part of Ser. No. 234,812, Apr. 28, 1994, Pat. No. 5,557,535.

[51] Int. Cl.$^6$ .............................. G06F 19/00; C07K 5/00; C07K 14/00
[52] U.S. Cl. ................................ 702/22; 702/19; 702/27; 530/300; 530/350
[58] Field of Search ..................................... 364/496, 578, 364/498, 499, 497; 434/278, 86, 89, 15, 43; 435/69.1, 219; 436/8, 15, 86; 395/119, 127, 137, 161, 920, 924; 702/22, 19, 27; 530/350, 300

[56] References Cited

U.S. PATENT DOCUMENTS

| | | | |
|---|---|---|---|
| 4,881,175 | 11/1989 | Ladner ..................................... | 364/496 |
| 4,908,773 | 3/1990 | Pantoliano et al. ...................... | 364/496 |
| 5,025,388 | 6/1991 | Cramer, III et al. .................... | 364/496 |
| 5,241,470 | 8/1993 | Lee et al. ................................. | 364/413 |
| 5,260,882 | 11/1993 | Blanco et al. ........................... | 364/499 |
| 5,307,287 | 4/1994 | Cramer, III et al. .................... | 364/496 |
| 5,420,805 | 5/1995 | Still et al. ................................. | 364/578 |
| 5,436,850 | 7/1995 | Eisenberg et al. ....................... | 364/496 |
| 5,557,535 | 9/1996 | Srinivasan et al. ...................... | 364/496 |

OTHER PUBLICATIONS

J. Moult and M.N.G. James. Proteins: Structure, Function and Genetics. 1:146–163 (1986), Dec. 1986.
W.R. Taylor. J. Mol. Biol. 188 233–258, 1986.
B.R. Brooks et al. Journal of Computational Chemistry vol. 4, No. 2, 187–217 (1983).
New Riverside University Dictionary, A.H. Soukhanov (Editor), The Riverside Publishing Company 1988.
Brooks et al., "CHARMM: A Program for Macromolecular Energy, Minimization, and Dynamics Calculations," *Journal of Computational Chemistry*, vol. 4, No. 2, 1983, pp. 187–217.
Srinivasan, Subhashini et al., "Multistep Modeling of Protein Structure: Application to Bungarotoxin," *International Journal of Quantum Chemistry: Quantum Biology Symposium* 13, 1986, pp. 167–174.
Havel, Timothy and Mark E. Snow, "A New Method For Building Protein Conformations From Sequence Alignments With Homologues of Known Structure," *J. Mol. Biol.*, 1991, pp. 1–7.
Srinivasan et al., "An Evaluation of the Performance of an Automated Procedure For Comparative Modeling of Protein Tertiary Structure," Protein Engineering, vol. 6, No. 5, pp. 501–512, 1993.
Baldi et al, "Hidden Markov Models of Biological Primary Sequence Information," Proceeding of the National Academy of Science, vol. 91, pp. 1059–1063, 1994.

*Primary Examiner*—Lila Feisee
*Assistant Examiner*—Nirmal S. Basi
*Attorney, Agent, or Firm*—Seed and Berry LLP

[57] ABSTRACT

A method in a computer system for modeling a three-dimensional structure of a model protein is provided. In one embodiment, the modeling is based upon a three-dimensional structure of a template protein and an amino acid sequence alignment of the model protein and the template protein. For each amino acid in the model protein, when the template protein has an amino acid aligned with the amino acid of the model protein, the position of the backbone atom of the amino acid of the model protein is established based on the position of a topologically equivalent backbone atom in the aligned amino acid of the template protein. In another embodiment, the modeling of a variable region of the model protein is based on a collection of ψ and φ angle values for amino acid pairs in a family of proteins. In a further embodiment, these ψ and φ angle values are classified according to a tetramer of adjacent amino acids and filtered based on a most probable conformation of portions of the variable region of the model protein.

18 Claims, 15 Drawing Sheets

Amino Acid Angle Matrix

Tetramer Matrix

METHOD AND SYSTEM FOR PROTEIN MODELING

CROSS-REFERENCE TO PRIOR APPLICATION

This application is a continuation-in-part of U.S. patent application Ser. No. 08/055,050, filed Apr. 28, 1993, which issued as U.S. Pat. No. 5,453,937 on Sep. 26, 1995 and which is hereby incorporated by reference, and U.S. patent application Ser. No. 08/234,812, filed Apr. 28, 1994, now U.S. Pat. No. 5,557,535, and which is hereby incorporated by reference.

TECHNICAL FIELD

This invention relates generally to a computer-implemented method and system for modeling the three-dimensional structure of a protein, and, more specifically, to protein modeling using $\psi$ and $\phi$ angle values collected from protein families (or structurally characterized proteins).

BACKGROUND OF THE INVENTION

The function of a protein is related to its three-dimensional structure. The three-dimensional structure of some proteins can be determined using X-ray crystallography or Nuclear Magnetic Resonance (NMR). However, for other proteins, these methods cannot be used to determine the three-dimensional structure. When these methods cannot be used, computer-based protein modeling techniques have been used with some success. These protein modeling techniques use the known three-dimensional structure of a homologous protein to approximate the structure of another protein.

In one such technique, the known three-dimensional structures of the proteins in a given family are superimposed to define the structurally conserved regions in that family. Among the members of a given family, there is considerable variation in the conformations of regions located between two consecutive structurally conserved regions, and thus, these regions are called the variable regions. These variable regions essentially contribute to the identity of a protein in its family. However, the modeling of the variable regions has been unsatisfactory.

Conventional homology modeling techniques have been used routinely to build models of proteases and antibodies. These techniques generally model the three-dimensional position of amino acids in structurally conserved regions by taking the Cartesian coordinates from homologous amino acids in a template protein with known three-dimensional structure. For the amino acids in the variable regions, these techniques take suitable loops from the Protein Data Bank (PDB). (The PDB is a collection of protein information relating to the known structure of protein. The PDB is administered by Brookhaven National Laboratory.) Although these techniques are generally successful in modeling the structurally conserved regions for structurally undefined members of the family, these techniques have been unsuccessful in modeling of the variable regions. Since variable regions and structurally conserved regions of the model protein come from different protein structures, high energy short contacts are often found in the models. These high energy contacts are usually between inter-variable regions that are grafted from different known protein structures. In cases where the sequence identity in the structurally conserved regions between the template and the model protein is weak, the interior amino acids are also susceptible to short contacts. Generally, these short contacts are removed by performing rotation around single bonds using interactive graphics, which is a tedious, and at times, an impractical procedure. Energy minimization has been used to relax strains in a model. However, the minimization procedure leads to structures that are trapped in local minima and relies entirely on the integrity of the starting structure.

Certain proteins with very weak sequence identities fold into similar three-dimensional structures. For example, the three-dimensional structures of a number of helical cytokines fold in similar three-dimensional topology in spite of weak sequence homology. Members of helical cytokine family not only show diversity in their disulfide topology but also the disulfide crosslinks are part of the variable regions. Besides the helical cytokines, there are other protein families with weak sequence identities and non-homologous disulfides in the variable regions. The prior homology modeling techniques produce unsatisfactory modeling of these families because of the absence of sequence homology in the structurally conserved regions and the presence of non-homologous disulfide crosslinks in the variable regions.

SUMMARY OF THE INVENTION

It is an object of the present invention to provide a method and system for modeling the three-dimensional structure of members of a protein family/superfamily from the known three-dimensional structure of one or more members of that family.

It is another object of the present invention to provide a method and system for modeling the three-dimensional structure of a protein by using position information of all topologically equivalent atoms in a template protein.

It is another object of the present invention to provide a method and system for generating a sequence alignment between two proteins based on the resulting three-dimensional structure model.

It is another object of the present invention to provide a method and system for generating a protein model that minimizes short contacts.

It is another object of the present invention to provide a method and system for modeling proteins with weak sequence identity with a template protein.

It is another object of the present invention to provide a method and system for modeling variable regions between two structurally conserved regions of a protein.

It is another object of the present invention to provide a method and system for modeling variable regions constrained by disulfide crosslinks of a protein.

These and other objects, which will become apparent as the invention is more fully described below, are provided by a computer-implemented method and system for modeling a three-dimensional structure of a model protein. In a preferred embodiment, the modeling is based upon a three-dimensional structure of a template protein and an amino acid sequence alignment of the model protein and the template protein. The proteins comprise a plurality of amino acids having backbone atoms and side chain atoms. For each amino acid in the model protein, when the template protein has an amino acid aligned with the amino acid of the model protein, the position of each backbone atom of the amino acid of the model protein is established based on the position of a topologically equivalent backbone atom in the aligned amino acid of the template protein. Then, the inter-atomic distance constraints for each pair of atoms with an established position is generated. Finally, the position of each atom in the model protein is set so that the inter-atomic distances are in accordance with the constraints.

In another aspect, the present invention provides for a method and system for modeling a three-dimensional structure of a variable region of a model protein. The model protein has amino acids that have positions within a three-dimensional structure. The method receives relative positional information between pairs of amino acids. The relative positional information preferably includes the $\psi$ and $\phi$ angle values between pairs of amino acids. The method then establishes a position for a first amino acid in the variable region. The method then for each amino acid pair in the variable region generates a model position for the amino acids based on the received relative positional information for the pair of amino acids. In a preferred embodiment the $\psi$ and $\phi$ angle values are collected for pairs of amino acid combinations in variable regions of a family of proteins. The generated model position for the amino acids are preferably based on a random selection of the collected $\psi$ and $\phi$ angle values.

In another aspect, the present invention provides a method in a computer system for generating a collection of relative positional information between pairs of amino acids for use in modeling a three-dimensional structure of a variable region of a model protein. The computer system has relative positional information between pairs of amino acids in the variable regions of a collection of proteins obtained from sources such as the PDB. The method classifies the amino acids that are downstream and upstream for each pair of amino acids in the variable regions of each protein in the collection of proteins. The method then stores the relative positional information for the amino acid pair based on the amino acids in the amino acid pair and on the classification of the amino acids that are downstream and upstream so that the position of each amino acid in the variable region of the model protein can be model based on the stored relative positional information.

The relative positional information is preferably the $\psi$ and $\phi$ angle values for the amino acid pair. The method also preferably classifies the adjacent amino acids as charged, hydrophobic, or polar. In addition, the method preferably filters the $\psi$ and $\phi$ angle values based on those values which contribute to the most probable conformation of the variable region to be modeled.

DETAILED DESCRIPTION OF THE INVENTION

Figure 1:
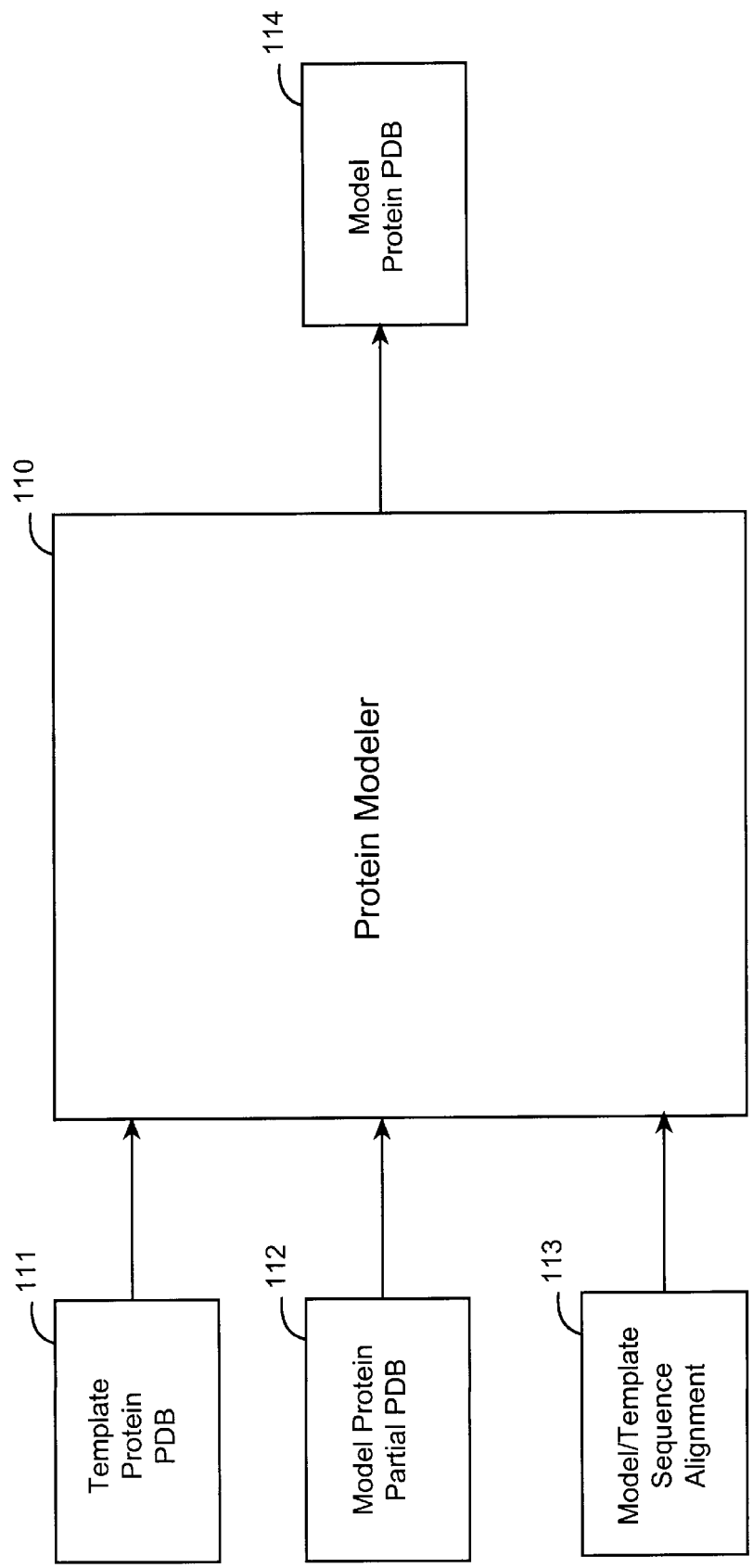
FIG. 1 is an overall block diagram of the input and output for the protein modeler.

The present invention provides a computer-based method and system for modeling the three-dimensional structure of a protein (model protein). In the following sections, descriptions of protein modeling based on sequence alignment and inter-atomic distance, based on $\psi$ and $\phi$ angles for dimers, and based on $\psi$ and $\phi$ angles based on tetramers are described.

Sequence Alignment and Inter-Atomic Distances

In a preferred embodiment, the protein modeler generates the three-dimensional structure of the model protein based on a template protein with a known three-dimensional structure and an amino acid sequence alignment between the model protein and the template protein. Using the template protein and the sequence alignment, the protein modeler generates a variety of inter-atom distance constraints for conserved regions and standard and chemical constraints for variable regions, and allows for the input of miscellaneous constraints (e.g., disulfide crosslinks). The protein modeler then generates a three-dimensional structure for the model protein using known techniques of distance geometry to ensure compliance with the constraints. Appendix A contains a further description of the present invention.

The protein modeler generates the inter-atomic distance constraints for the model protein based on the position of topologically equivalent atoms (TEA) in the template protein. The protein modeler determines whether each atom in the model protein is topologically equivalent to an atom in the template protein. An atom of an amino acid of the model protein is topologically equivalent when the amino acid of the model protein aligns with an amino acid of the template protein and the amino acid of the template protein has a corresponding atom. If the aligned amino acids are identical, then each atom of the model amino acid corresponds to the atom of the same name in the template amino acid. For example, the C-alpha atom of the model amino acid corresponds to the C-alpha atom of the template amino acid, and the C-beta atom of the model amino acid corresponds to the C-beta atom of the template amino acid. If the aligned amino acids are not identical, then each atom of the model amino acid may or may not have a corresponding atom in the template amino acid. Each backbone atom (N, C-alpha, C', and O) has a corresponding atom. However, the correspondence between side chain atoms depends on the aligned amino acids. For example, if the model amino acid is arginine and the template amino acid is alanine, then the C-beta atoms correspond. However, the C-gamma, C-delta, and other atoms of the arginine side chain have no corresponding atoms in the alanine side chain.

The protein modeler sets the position of each topologically equivalent atom in the model protein to the same position as that of the topologically equivalent atom in the template protein. The protein modeler then calculates the distance between each pair of atoms that have topologically equivalent atoms. These distances are the inter-atomic distance constraints for the topologically equivalent atoms in the model protein. In one embodiment, these distance constraints can be relaxed by accounting for the overall homology between the model and template protein as discussed below.

The protein modeler generates standard constraints based on the planarity of a side chain, the C-alpha and C-beta chirality, and C-alpha inter-atomic distances.

In a preferred embodiment, the protein modeler assigns a helical conformation to each amino acid in the model protein and establishes a position for each atom. The protein modeler then uses well-known software packages to generate chemical constraints such as inter-atomic distances between 1–2 and 1–3 neighbors based on the connectivity of the model protein. The inter-atomic distance constraints are used to constrain the topology relating to non-topologically equivalent atoms (non-TEAs). The selection of a helical conformation is arbitrary and used to establish position information for the standard software package. One skilled in the art would appreciate that one could generate such 1–2 and 1–3 neighbor constraints without use of standard software packages, and, thus obviate the need to establish the position of each atom to generate these constraints.

Once the various constraints are established, the well-known distance geometry software, DGEOM (discussed below), is invoked to calculate the position of each atom in the model protein and thus generates the three-dimensional structure of the model protein.

FIG. 1 is an overall block diagram of the input and output for the protein modeler. The protein modeler 110 is preferably implemented on a computer system. In a preferred embodiment, the protein modeler 110 inputs template protein structure 111, the model protein partial structure 112, and the model/template protein sequence alignment. Based on the input information, the protein modeler generates a model protein structure 114. The format of the information defining the protein structures are in a format defined by the Protein Data Bank (PDB). Table 1 on the following page illustrates the PDB protein structure format.

TABLE 1

| | | Atom Portion | | | | |
|---|---|---|---|---|---|---|
| | iAtom | Atom | AA | iAA | X | Y | Z |
| ATOM | 1 | N | ALA | 1 | 0.000 | 0.000 | 0.000 |
| ATOM | 2 | CA | ALA | 1 | 0.762 | −1.174 | 0.000 |
| ATOM | 3 | C | ALA | 1 | 0.638 | −2.028 | 1.220 |
| ATOM | 4 | O | ALA | 1 | 0.589 | −3.333 | 1.099 |
| ATOM | 5 | CB | ALA | 1 | 2.256 | −0.891 | −0.123 |
| ATOM | 6 | N | ASP | 2 | 0.569 | −1.403 | 2.560 |
| ATOM | 7 | CA | ASP | 2 | 0.449 | −2.161 | 3.767 |
| ATOM | 8 | C | ASP | 2 | −0.904 | −2.875 | 3.745 |
| ATOM | 9 | O | ASP | 2 | −0.955 | −4.068 | 4.177 |
| ATOM | 10 | CB | ASP | 2 | 0.524 | 1.274 | 4.963 |
| ATOM | 11 | CG | ASP | 2 | 1.899 | −0.662 | 5.163 |
| ATOM | 12 | OD1 | ASP | 2 | 2.906 | −1.088 | 4.803 |
| ATOM | 13 | OD2 | ASP | 2 | 1.801 | 0.439 | 5.828 |
| ATOM | 14 | N | LEU | 3 | 2.104 | −2.178 | 3.231 |
| ATOM | 15 | CA | LEU | 3 | −3.297 | −2.981 | 3.276 |
| ATOM | 16 | C | LEU | 3 | −3.207 | −4.201 | 2.341 |
| ATOM | 17 | O | LEU | 3 | −3.650 | −5.307 | 2.689 |
| ATOM | 18 | CB | LEU | 3 | −4.529 | −2.195 | 2.856 |
| ATOM | 19 | CG | LEU | 3 | −4.792 | −0.924 | 3.666 |
| ATOM | 20 | CD1 | LEU | 3 | −6.093 | −0.212 | 3.337 |
| ATOM | 21 | CD2 | LEU | 3 | −4.699 | −1.311 | 5.152 |
| ATOM | 22 | N | GLU | 4 | −2.587 | −4.068 | 1.004 |
| ATOM | 23 | CA | GLU | 4 | −2.545 | −5.304 | 0.168 |

TABLE 1-continued

| ATOM | 24 | C | GLU | 4 | −1.631 | −6.304 | 0.886 |
|---|---|---|---|---|---|---|---|
| ATOM | 25 | O | GLU | 4 | −1.925 | −7.494 | 0.922 |
| ATOM | 26 | CB | GLU | 4 | −1.990 | −5.001 | −1.237 |

| | | Connectivity Portion | | | |
|---|---|---|---|---|---|
| | | neighbor[1] | neighbor[2] | neighbor[3] | neighbor[4] |
| CONECT | 1 | 2 | 0 | 0 | 0 |
| CONECT | 2 | 1 | 3 | 5 | 0 |
| CONECT | 3 | 2 | 4 | 6 | 0 |
| CONECT | 4 | 3 | 0 | 0 | 0 |
| CONECT | 5 | 2 | 0 | 0 | 0 |
| CONECT | 6 | 7 | 3 | 0 | 0 |
| CONECT | 7 | 6 | 8 | 10 | 0 |
| CONECT | 8 | 7 | 9 | 14 | 0 |
| CONECT | 9 | 8 | 0 | 0 | 0 |
| CONECT | 10 | 7 | 11 | 0 | 0 |
| CONECT | 11 | 10 | 12 | 13 | 0 |
| CONECT | 12 | 11 | 0 | 0 | 0 |
| CONECT | 13 | 1I | 0 | 0 | 0 |
| CONECT | 14 | 15 | g | 0 | 0 |
| CONECT | 15 | 14 | 16 | 18 | 0 |
| CONECT | 16 | 15 | 17 | 22 | 0 |
| CONECT | 17 | 16 | 0 | 0 | 0 |

Table 1 contains an atom portion and a connectivity portion. The atom portion specifies for each atom in the protein a sequential atom number (iAtom), the atom name (Atom), the containing amino acid name (AA), the containing amino acid sequence number (iAA), and the Cartesian coordinates (position) of the atom (X,Y,Z). The connectivity portion indicates the connectivity of the atoms in the protein. The connectivity specifies each of the (up to four) neighbors of an atom.

Figure 2:
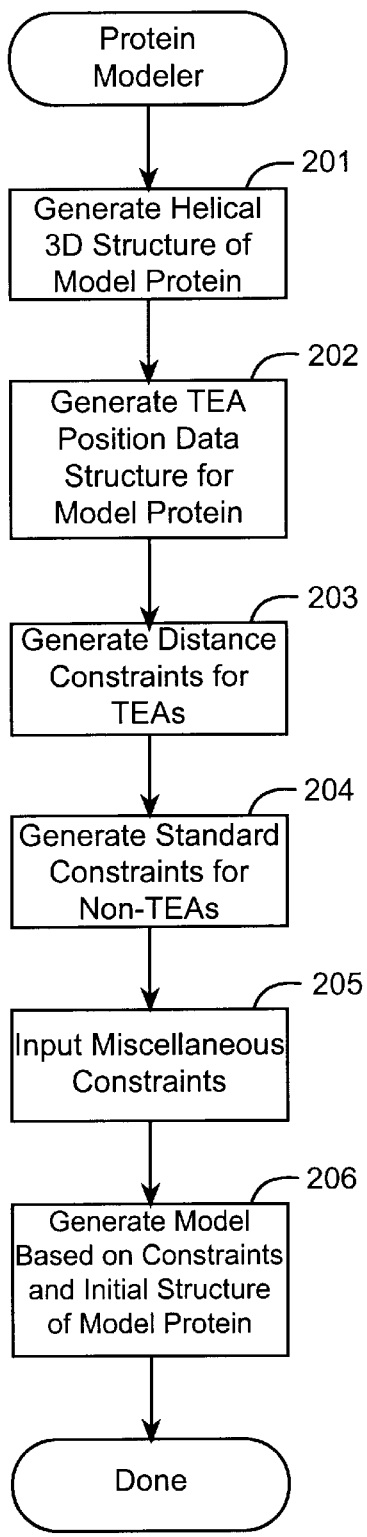
FIG. 2 is an overall flow diagram of the protein modeler.

FIG. 2 is an overall flow diagram of the protein modeler. In step 201, the protein modeler generates an initial three-dimensional structure for the model protein. In a preferred embodiment, the protein modeler inputs model protein partial structure 112, which contains structure information in PDB format without position information. One skilled in the art would appreciate that the model protein partial structure 112 could be generated by the protein modeler based on the model protein amino acid sequence. The position information for each atom in the model protein is generated based on a helical conformation. This position information is used by DGEOM to determine chemical constraints between the atoms of the model protein. These chemical constraints are later used to constrain the position of non-topologically equivalent atoms. The arbitrary assignment of helical conformation to the peptide backbone and the choice of side chain rotamers does not impose any restriction on subsequent stages of the modeling procedure. In fact, non-helical conformations can also produce acceptable results. An acceptable helical conformation algorithm may be found Sundaram, K. and Srinivasan, S., Computer Programs Biomed, "Computer Simulated Modeling of Biomolecular Systems," Vol. 10, p. 29–34, 1979. As discussed above, this step is used to take advantage of predefined software packages that generate chemical constraints. However, the chemical constraints could be generated directly from the model protein amino acid sequence based on well-known chemical constraint principles such as 1–2 and 1–3 neighbor topology.

In step 202, the protein modeler generates a TEA position data structure for the model protein based on topologically equivalent atoms. The sequence alignment between the template and the model protein is used to generate the TEA position data structure for the protein model. The protein modeler retrieves the position information for each topologically equivalent atom in the template protein and stores the result in the TEA position data structure for the model protein. The protein modeler also indicates in the TEA position data structure which atoms have no topologically equivalent atom in the template protein. Table 2 illustrates a sample TEA position data structure (also known as a hybrid data structure because it contains information based on the model and template proteins). The TEA position data structure contains an entry for each atom in the model protein. Each entry contains the following fields. The derived field contains a 'T' for a topologically equivalent atom and an 'M' for a non-topologically equivalent atom. The fields model amino acid number (miAA), model amino acid name (mAA), model atom number (miAtom), and model atom name (mAtom) identify the atom of the model protein. The fields template amino acid number (tiAA), template amino acid name (tAA), template atom number (tiAtom), and template atom name (tAtom) identify the topologically equivalent atom in the template protein. The fields X, Y, and Z specify the position of a topologically equivalent atom.

allow for the methods of the present invention to be expanded to include other constraints as they become known. For example, a miscellaneous constraint could be distance constraints imposed by disulfide crosslinks. In step 206, the protein modeler generates the three-dimensional structure for the model protein based on the constraints and the helical three-dimensional structure of the model protein. The protein modeler preferably employs the well-known program DGEOM to generate the three-dimensional structure for the model protein. The DGEOM program is one of various well-known programs that are based on the principles of distance geometry. Appendix B contains a description of DGEOM. A detailed explanation of the theory in practice of distance geometry can be found in Havel, T. F., Kuntz, I. D., and Crippen, G. M., Bull. Math Biol., "Theory and Practice of Distance Geometry," Vol. 45, pp. 666–720, 1983.

Figure 3:
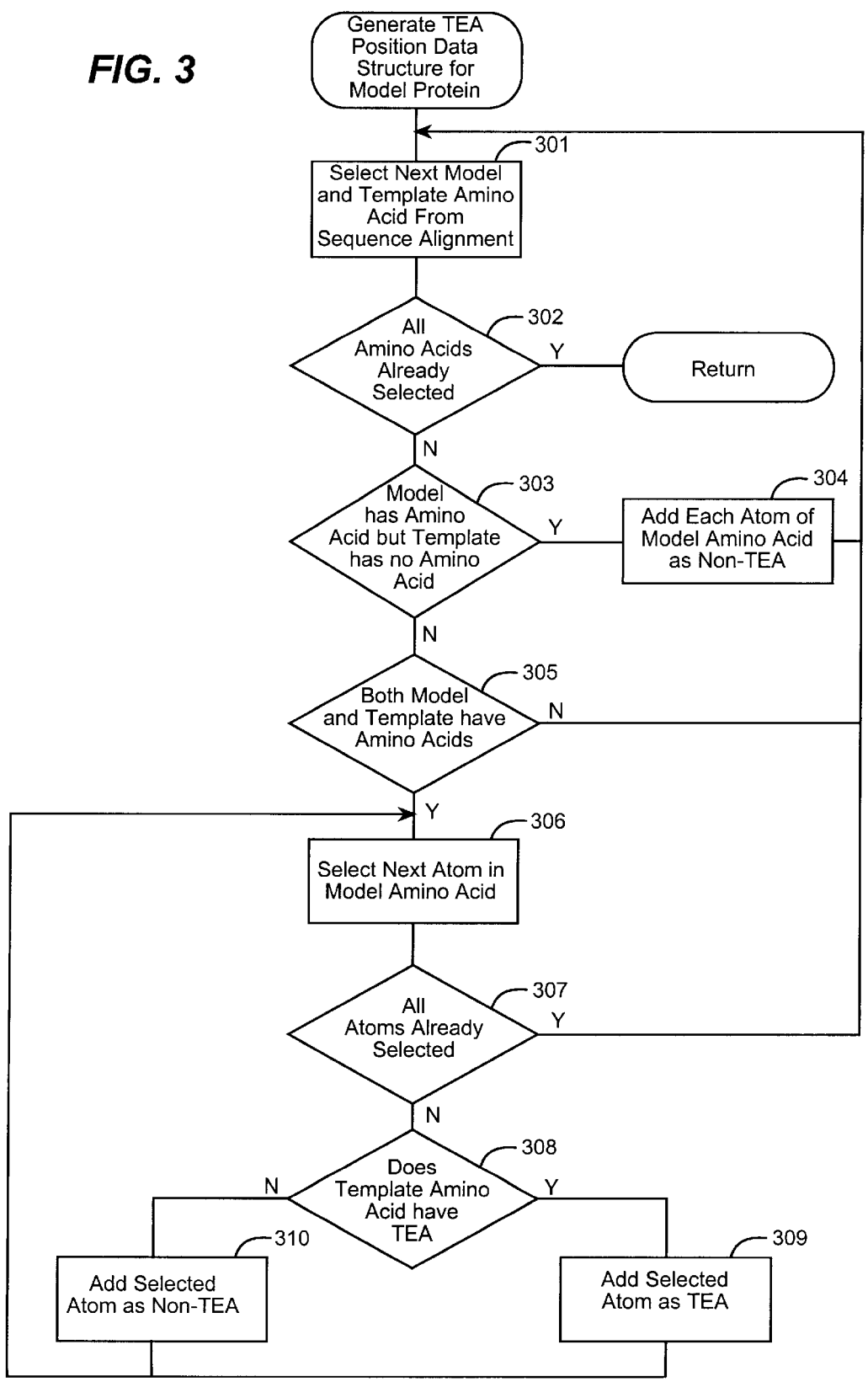
FIG. 3 is a flow diagram of a routine to generate a TEA position data structure for the model protein.

FIG. 3 is a flow diagram of a routine to generate a TEA position data structure for the model protein. This routine inputs the model and template sequence alignment and the three-dimensional structure of template protein, and outputs

TABLE 2

| derived | miAA | mAA | miAtom | mAtom | tiAA | tAA | tiAtom | tAtom | X | Y | Z |
|---|---|---|---|---|---|---|---|---|---|---|---|
| T | 1 | ALA | 1 | N | 9 | LYS | 65 | N | 2.905 | 16.102 | 16.260 |
| T | 1 | ALA | 2 | CA | 9 | LYS | 66 | CA | 3.912 | 15.058 | 16.725 |
| T | 1 | ALA | 3 | C | 9 | LYS | 67 | C | 5.266 | 15.385 | 16.010 |
| T | 1 | ALA | 4 | O | 9 | LYS | 68 | O | 6.290 | 15.212 | 16.692 |
| T | 1 | ALA | 5 | CB | 9 | LYS | 69 | CB | 3.466 | 13.692 | 16.221 |
| T | 2 | ASP | 6 | N | 10 | LEU | 74 | N | 5.295 | 15.639 | 14.727 |
| T | 2 | ASP | 7 | CA | 10 | LEU | 75 | CA | 6.466 | 16.097 | 13.966 |
| T | 2 | ASP | 8 | C | 10 | LEU | 76 | C | 7.251 | 17.154 | 14.667 |
| T | 2 | ASP | 9 | O | 10 | LEU | 77 | O | 8.444 | 17.104 | 15.130 |
| T | 2 | ASP | 10 | CB | 10 | LEU | 78 | CB | 6.037 | 16.475 | 12.514 |
| T | 2 | ASP | 11 | CG | 10 | LEU | 79 | CG | 7.066 | 16.512 | 11.446 |
| T | 2 | ASP | 12 | OD1 | 10 | LEU | 80 | CD1 | 6.325 | 16.645 | 10.067 |
| T | 2 | ASP | 13 | OD2 | 10 | LEU | 81 | CD2 | 7.874 | 17.787 | 11.570 |
| T | 3 | LEU | 14 | N | 11 | ARG | 82 | N | 6.616 | 18.280 | 14.857 |
| T | 3 | LEU | 15 | CA | 11 | ARG | 83 | CA | 7.108 | 19.506 | 15.459 |
| T | 3 | LEU | 16 | C | 11 | ARG | 84 | C | 7.571 | 19.194 | 16.881 |
| T | 3 | LEU | 17 | O | 11 | ARG | 85 | O | 8.732 | 19.516 | 17.254 |
| T | 3 | LEU | 18 | CB | 11 | ARG | 86 | CB | 6.052 | 20.688 | 15.582 |
| T | 3 | LEU | 19 | CG | 11 | ARG | 87 | CG | 6.569 | 21.939 | 16.339 |
| T | 3 | LEU | 20 | CD1 | 11 | ARG | 88 | CD | 5.524 | 23.079 | 16.429 |
| M | 3 | LEU | 21 | CD2 | | | | | | | |
| T | 4 | GLU | 22 | N | 12 | GLN | 93 | N | 6.717 | 18.621 | 17.675 |
| T | 4 | GLU | 23 | CA | 12 | GLN | 94 | CA | 7.107 | 18.413 | 19.062 |
| T | 4 | GLU | 24 | C | 12 | GLN | 95 | C | 8.174 | 17.335 | 19.110 |
| T | 4 | GLU | 25 | O | 12 | GLN | 96 | O | 8.879 | 17.329 | 20.161 |
| T | 4 | GLU | 26 | CB | 12 | GLN | 97 | CB | 5.948 | 18.162 | 20.019 |
| T | 4 | GLU | 27 | CG | 12 | GLN | 98 | CG | 5.015 | 19.373 | 20.013 |
| T | 4 | GLU | 28 | CD | 12 | GLN | 99 | CD | 3.833 | 19.168 | 21.006 |
| T | 4 | GLU | 29 | OE1 | 12 | GLN | 100 | OE1 | 3.439 | 18.011 | 21.258 |
| T | 4 | GLU | 30 | OE2 | 12 | GLN | 101 | NE2 | 3.240 | 20.354 | 21.278 |
| T | 5 | ASP | 31 | N | 13 | GLY | 102 | N | 8.109 | 16.289 | 18.305 |
| T | 5 | ASP | 32 | CA | 13 | GLY | 103 | CA | 9.140 | 15.202 | 18.416 |
| T | 5 | ASP | 33 | C | 13 | GLY | 104 | C | 10.525 | 15.821 | 17.951 |
| T | 5 | ASP | 34 | O | 13 | GLY | 105 | O | 11.502 | 15.199 | 18.495 |
| T | 5 | ASP | 35 | CB | | | | | | | |
| T | 5 | ASP | 36 | CG | | | | | | | |
| T | 5 | ASP | 37 | OD1 | | | | | | | |
| T | 5 | ASP | 38 | OD2 | | | | | | | |

In step 203, the protein modeler generates the distance constraints based on the TEA position data structure. The protein modeler determines the distance between each topologically equivalent atom. In step 204, the protein modeler generates standard constraints for non-topologically equivalent atoms. These standard constraints include planarity of side chains, 1–4 inter-C-alpha distances, and C-alpha and C-beta chirality. In step 205, the protein modeler inputs miscellaneous constraints. These miscellaneous constraints the TEA position data structure for the model protein. In step 301, the routine selects the next model and template amino acid from the sequence alignment. In step 302, if all the amino acids have already been selected, then the routine returns, else the routine continues at step 303. In step 303, if the model protein has an amino acid in the sequence position but the template protein has no amino acid, then the amino acid is part of a variable region and the routine continues at step 304, else the routine continues at step 305.

In step 304, the routine adds an entry to the TEA position data structure for each atom of the model amino acid as a non-topologically equivalent atom and loops to step 301 to select the next amino acid in the sequence alignment. In step 305, if both the model and template proteins have an amino acid in the sequence alignment, then the routine continues at step 306 to determine which atoms between the amino acids are topologically equivalent, else the routine loops to step 301. In step 306, the routine selects the next atom in the model amino acid starting with a first atom. In step 307, if all the atoms in the model amino acid have already been selected, then the routine loops to step 301, else the routine continues at step 308. In step 308, if the template amino acid has a topologically equivalent atom to the selected atom of the model amino acid, then the routine continues at step 309, else the routine continues at step 310. In step 309, the routine adds an entry to the TEA position data structure for the selected atom as a topologically equivalent atom and loops to step 306. In step 310, the routine adds an entry to the TEA position data structure for the selected atom as a non-topologically equivalent atom and the routine loops to step 306.

CODE TABLE 1

```
void GenerateTEAPositionDataStructure()
{
  imAtom = 1;
  itAtom = 1;
  for (i=1; i<=cAminoAcids; i++)
    {tAA = Align[i].tAA;
     mAA = Align[i].mAA;
     if (tAA = '-' && mAA != '-')
        AddVarAA();
     if (tAA != "-" && mAA != "-")
        {for (j=1; j<=cmaxAtoms; j++)
           if (PIM[mAA][j] == 1
              if (PIM[tAA][j] == 1)
                 AddTEA(imAtom++, itAtom++);
              else
                 AddNTEA(imAtom++);
        }
    }
}
void AddVarAA()
{
  do
     AddNTEA(imAtom++);
  while (Helical[imAtom].iAA == Helical[imAtom-1].iAA)
}
void AddNTEA(index x)
{
  Hybrid[x].derived   = "M";
  Hybrid[x].imAA      = Helical[x].iAA;
  Hybrid[x].mAA       = Helical[x].AA;
  Hybrid[x].imAtom    = Helical[x].iAtom;
  Hybrid[x].mAtom     = Helical[x].Atom;
```

CODE TABLE 1-continued

```
}
void AddTEA(index x, y)
{
  Hybrid[x].derived   = "T";
  Hybrid[x].imAA      = Helical[x].iAA;
  Hybrid[x].mAA       = Helical[x].AA;
  Hybrid[x].imAtom    = Helical[x].iAtom;
  Hybrid[x].mAtom     = Helical[x].Atom;
  Hybrid[x].itAA      = Templat[y].iAA;
  Hybrid[x].tAA       = Templat[y].AA;
  Hybrid[x].itAtom    = Templat[y].iAtom;
  Hybrid[x].tAtom     = Templat[y].Atom;
  Hybrid[x].x         = Templat[y].x;
  Hybrid[x].y         = Templat[y].y;
  Hybrid[x].z         = Templat[y].z;
}
```

Code Table 1 contains "C" programming language pseudocode corresponding to the flow diagram of FIG. 3. The data structure Align contains the protein sequence alignment. The data structure Helical contains data relating to the three-dimensional structure of a helical conformation of the model protein. However, the pseudocode does not use the helical position data. The data structure Template contains the data relating to the three-dimensional structure of the template protein. The data structure Hybrid contains the TEA position data structure. The fields names are the same as described above for the three-dimensional structure in PDB format and the TEA positional data structure. The pseudocode also uses the position identity matrix (PIM) defined in Table 3.

Table 3 is the position identity matrix for side chain atoms of amino acids. The rows of table 3 represent amino acids and the columns represent positional identity of the amino acids. Topologically equivalent atoms in different amino acids are aligned in columns with an entry of 1. For example, if alanine is replaced by arginine in the model, the position of the arginine atoms—N, C-alpha, C', O, and C-beta—in the template protein are used. Although not shown, the position identity matrix also contains columns for each of the four backbone atoms.

TABLE 3

|     | B (5) | G1 (6) | G2 (7) | D1 (8) | D2 (9) | E1 (10) | E2 (11) | E3 (12) | Z1 (13) | Z2 (14) | Z3 (15) | H1 (16) | H2 (17) |
|-----|---|---|---|---|---|---|---|---|---|---|---|---|---|
| Ala | 1 | 0 | 0 | 0 | 0 | 0 | 0 | 0 | 0 | 0 | 0 | 0 | 0 |
| Arg | 1 | 1 | 0 | 1 | 0 | 1 | 0 | 0 | 1 | 0 | 0 | 1 | 1 |
| Asn | 1 | 1 | 0 | 1 | 1 | 0 | 0 | 0 | 0 | 0 | 0 | 0 | 0 |
| Asp | 1 | 1 | 0 | 1 | 1 | 0 | 0 | 0 | 0 | 0 | 0 | 0 | 0 |
| Cys | 1 | 1 | 0 | 0 | 0 | 0 | 0 | 0 | 0 | 0 | 0 | 0 | 0 |
| Glu | 1 | 1 | 0 | 1 | 0 | 1 | 1 | 0 | 0 | 0 | 0 | 0 | 0 |
| Gln | 1 | 1 | 0 | 1 | 0 | 1 | 1 | 0 | 0 | 0 | 0 | 0 | 0 |
| Gly | 0 | 0 | 0 | 0 | 0 | 0 | 0 | 0 | 0 | 0 | 0 | 0 | 0 |
| His | 1 | 1 | 0 | 1 | 1 | 1 | 1 | 0 | 0 | 0 | 0 | 0 | 0 |
| Ile | 1 | 1 | 1 | 1 | 0 | 0 | 0 | 0 | 0 | 0 | 0 | 0 | 0 |

TABLE 3-continued

|     | B (5) | G1 (6) | G2 (7) | D1 (8) | D2 (9) | E1 (10) | E2 (11) | E3 (12) | Z1 (13) | Z2 (14) | Z3 (15) | H1 (16) | H2 (17) |
|-----|-------|--------|--------|--------|--------|---------|---------|---------|---------|---------|---------|---------|---------|
| Leu | 1 | 1 | 0 | 1 | 1 | 0 | 0 | 0 | 0 | 0 | 0 | 0 | 0 |
| Lys | 1 | 1 | 0 | 1 | 0 | 1 | 0 | 0 | 1 | 0 | 0 | 0 | 0 |
| Met | 1 | 1 | 0 | 1 | 0 | 1 | 0 | 0 | 0 | 0 | 0 | 0 | 0 |
| Phe | 1 | 1 | 0 | 1 | 1 | 1 | 1 | 0 | 0 | 0 | 0 | 0 | 0 |
| Pro | 1 | 1 | 0 | 1 | 0 | 0 | 0 | 0 | 0 | 0 | 0 | 0 | 0 |
| Ser | 1 | 1 | 0 | 0 | 0 | 0 | 0 | 0 | 0 | 0 | 0 | 0 | 0 |
| Thr | 1 | 1 | 1 | 0 | 0 | 0 | 0 | 0 | 1 | 0 | 0 | 0 | 0 |
| Trp | 1 | 1 | 0 | 1 | 1 | 1 | 1 | 1 | 0 | 1 | 1 | 1 | 0 |
| Tyr | 1 | 1 | 0 | 1 | 1 | 1 | 1 | 0 | 1 | 0 | 0 | 1 | 0 |
| Val | 1 | 1 | 1 | 0 | 0 | 0 | 0 | 0 | 0 | 0 | 0 | 0 | 0 |

Figure 4:
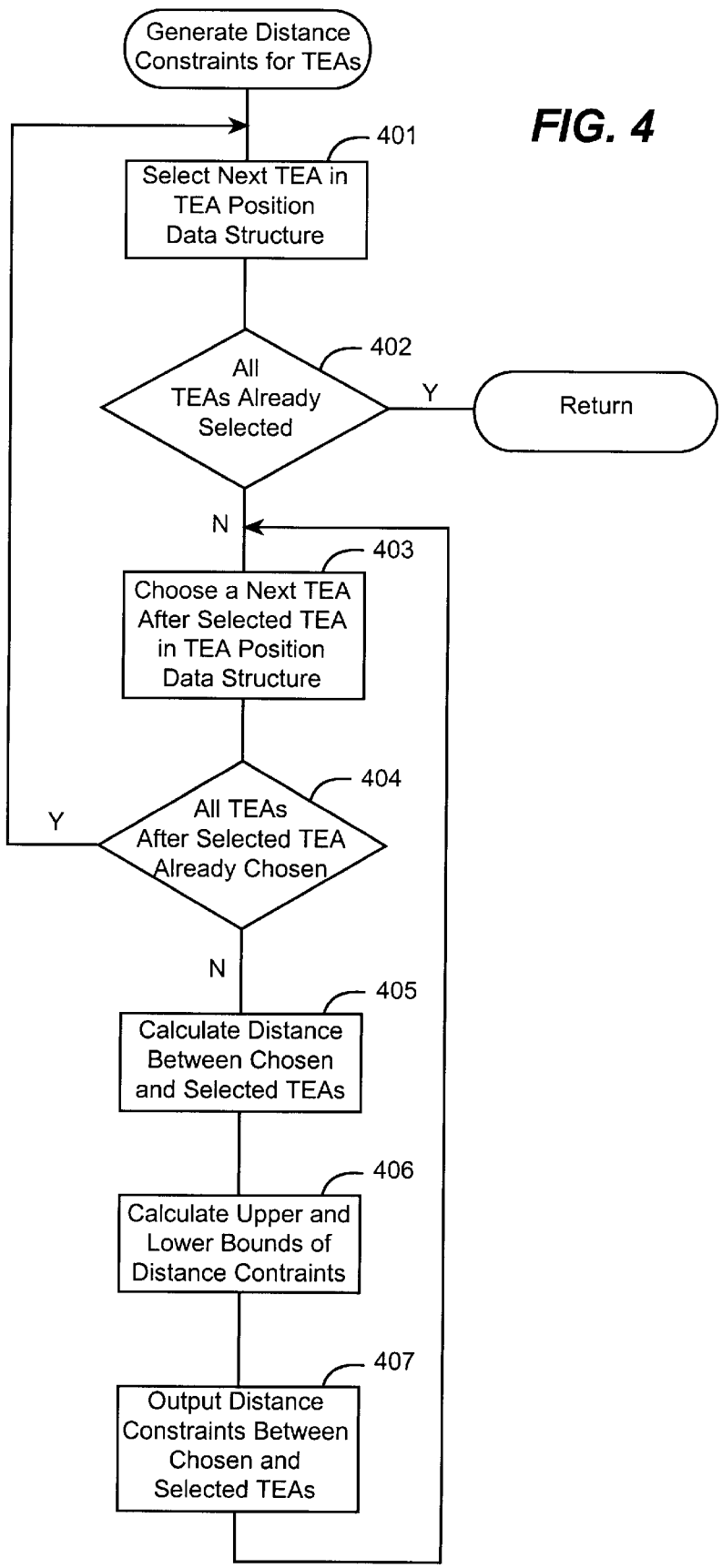
FIG. 4 is a routine to generate distance constraints for topologically equivalent atoms.

FIG. 4 is a flow diagram of the routine to generate distance constraints for topologically equivalent atoms. The routine inputs the TEA position data structure of the model protein and outputs distance constraints for the topologically equivalent atoms. In step 401, the routine selects the next topologically equivalent atom in the TEA position data structure, starting with the first topologically equivalent atom. In step 402, if all the topologically equivalent atoms have already been selected, then the routine returns, else the routine continues at step 403. In steps 403 through 407, the routine loops determining the distance between the selected topologically equivalent atom and all other topologically equivalent atoms. In step 403, the routine chooses a next topologically equivalent atom after the selected topologically equivalent atom in the TEA position data structure. In step 404, if all the topologically equivalent atoms after the selected topologically equivalent atom have already been chosen, then the routine loops to step 401 to select another topologically equivalent atom, else the routine continues at step 405. In step 405, the routine calculates the distance between the chosen and selected topologically equivalent atoms. In step 406, the routine calculates the upper and lower bounds of the distance constraints. As discussed above, the upper and lower bounds can be relaxed based on the overall homology between the model and template proteins. In step 407, the routine outputs the distance constraints between the chosen and the selected topologically equivalent atoms and the routine loops to step 403. Code Table 2 contains "C" programming language pseudocode for the flow diagram of FIG. 4.

CODE TABLE 2

```
void GenerateTEAconstraints()
{
    for (i=1; i<=nmAtoms; i++)
        if (Hybrid[i].derived == "T")
            for (j=i; j<=nmAtoms; j++)
                if (Hybrid[j].derived = "T")
                    {Calculate distance between atom i and j
                     Output mAA and mAtom for i and j
                         upper and lower bounds of distance
                    };
}
```

Figure 5:
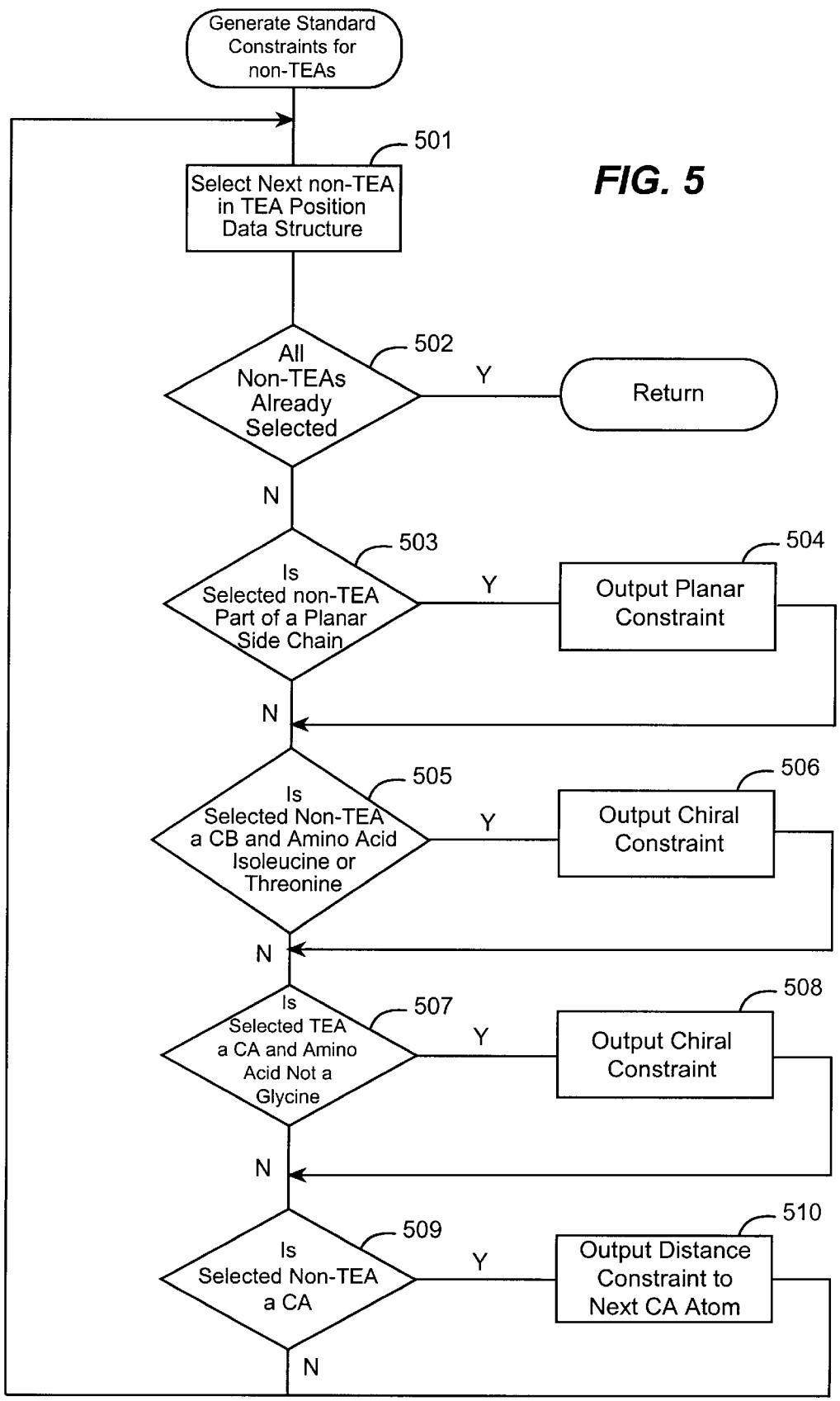
FIG. 5 is a routine to generate standard constraints for non-topologically atoms.

FIG. 5 is a flow diagram of a routine to generate standard constraints for non-topologically equivalent atoms. The routine inputs the TEA position data structure and outputs the standard constraints for non-topologically equivalent atoms. In step 501, the routine selects the next non-topologically equivalent atom in the TEA position data structure, starting with the first non-topologically equivalent atom. In step 502, if all the non-topologically equivalent atoms have already been selected, then the routine returns, else the routine continues at step 503. In step 503, if the selected non-topologically equivalent atom is part of a planar side chain, then the routine outputs a planar constraint in step 504 and continues at step 505. In step 505, if the selected non-topologically equivalent atom is a C-beta atom and the amino acid is isoleucine or threonine, then the routine outputs a C-beta chiral constraint in step 506 and continues at step 507. In step 507, if the selected non-topologically equivalent atom is a C-alpha atom and the amino acid is not glycine, then the routine outputs a C-alpha chiral constraint in step 508 and continues at step 509. In step 509, if the selected non-topologically equivalent atom is a C-alpha atom, then the routine outputs the distance constraints for the next C-alpha atom in the peptide chain. The routine then loops to step 501 to select the next non-topologically equivalent atom. Code Table 3 contains "C" programming language pseudocode for the flow diagram of FIG. 5.

CODE TABLE 3

```
void GenerateNTEAConstraints()
{
    for (i=1; i<nmAtoms; i++)
        if (Hybrid[i].derived = model)
            {if (Hybrid[i].mAA is planar)
                Output ("plane", ids of atoms in plane);
            if (Hybrid.mAtom is CB &&
                    Hybrid[i].mAA is isoleucine or threonine)
                Output ("chiral", ids of side chain atoms,
                    chiral volume);
            if (Hybrid[i].mAtom is CA &&
                    Hybrid[i].mAA is not glycine)
                Output ("chiral", id of CA atom,
                    ids of side chain atoms, chiral volume);
            if (Hybrid[i].mAtom is CA)
                Output (id of i atom, id of next CA atom,
                    upper and lower distance bound);
            }
}
```

Figure 6:
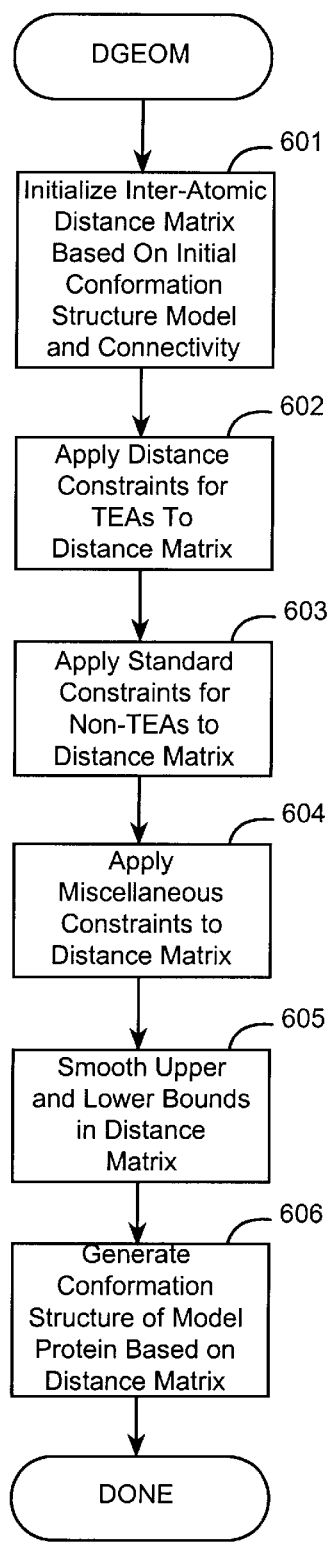
FIG. 6 is a flow diagram showing the DGEOM process.

FIG. 6 is a flow diagram of the utilization of the DGEOM software package. In step 601, DGEOM initializes an inter-atomic distance matrix based on the helical three-dimensional structure of the model protein. DGEOM determines inter-atomic distances based on chemical constraints such as inter-atomic distances between 1–2 and 1–3 neighbors. Although DGEOM establishes these distance constraints for all atoms within the model protein, the distance constraints for topologically equivalent atoms are eventually overridden by distance constraints imposed by the template protein. In step 602, DGEOM applies the distance constraints for the topologically equivalent atoms to the distance matrix. In step 603, DGEOM applies the standard constraints for non-topologically equivalent atoms to the distance matrix. In step 604, the routine applies miscellaneous constraints to the distance matrix. In step 605, DGEOM smoothes the upper and lower bounds in the distance matrix. In step 606, DGEOM generates the final three-dimensional structure of the model protein based on the smoothed distance matrix.

The following example illustrates the methods of the present invention. Table 4 contains a sequence alignment for the murine interleukin-4 (SEQ ID NO:1) and human interleukin-4 (SEQ ID NO:2) proteins. In this example, the three-dimensional structure of the human interleukin-4 (SEQ ID NO:2) protein is known, and the three-dimensional structure of the murine interleukin-4 (SEQ ID NO:1) (the model protein) protein is to be modeled. In this example, a template protein (SEQ ID NO:3) is derived from the human interleukin-4 protein (SEQ ID NO:2). The variable regions in the template protein are preferably expanded to allow for flexibility in modeling the transitions between conserved and variable regions.

Continuing with the example, the protein modeler sets the position of each atom in the model protein with a topologically equivalent atom in the template protein to the position of the atom in the template protein. For example, the first aligned amino acids for these model and template proteins are both leucine. Since each atom in the model amino acid has a topologically equivalent atom in the template amino acid, the protein modeler sets the position of each atom. Once the position of each topologically equivalent atom in the model protein is established, then the protein modeler generates the inter-atomic distance constraints for each pair of atoms. The protein modeler then determines standard constraints for the non-topologically equivalent atoms. For example, since the first amino acid, histidine, in the model protein does not align with an amino acid in the template protein, each atom of histidine is a non-topologically equivalent atom. Thus, a planar constraint, a C-alpha chiral constraint, and an inter-C-alpha distance constraint are generated. The protein modeler then inputs miscellaneous constraints that are generated by a user of the protein modeler. These constraints may typically be based on disulfide crosslinks or other empirically determined constraints. The protein modeler also generates chemical constraints for the non-topologically equivalent atom. Finally, the protein modeler applies all the constraints using the principles of the distance geometry to arrive at a three-dimensional structure of the murine interleukin-4 protein.

deviation, called a "divergence factor," is expressed by specifying that inter-atomic distances as ranges rather than a single value. These ranges allow the modeling to accommodate for differences between aligned amino acids that are not identical. That is, the position of the backbone atoms can be adjusted to accommodate the differences in the side chains.

In one embodiment, all inter-atomic distances between pairs of atoms are allowed to deviate within the divergence factor. In particular, the inter-atomic distances between atoms in the same structurally conserved region are allowed to deviate (intra-region deviation), and the inter-atomic distances between atoms in different structurally conserved regions are allowed to deviate (inter-region deviation). Alternatively, intra-region deviation is not allowed. By not allowing intra-region deviations, the backbone of each structurally conserved region is held rigid but is allowed to rotate relative to other structurally conserved regions.

In this alternate embodiment, the protein modeler generates a three-dimensional structure of the model protein based on a template protein with a known three-dimensional structure, an amino acid sequence alignment between the model protein and the template protein, and an identification of the structurally conserved regions. Since the sequence identity between the model protein and the template protein is assumed to be weak, accurate alignment and identification of structurally conserved regions can be achieved by the well-known techniques, such as, "secondary structure prediction" or "disulphide topology."

To model a divergent protein, the protein modeler performs several modeling iteration with various divergence factors. After each iteration, the number of distance violations for that iteration is recorded. A distance violation preferably occurs when a distance constraint cannot be satisfied to within a margin of error, which is 0.5 Å. The margin of error can be increased or decreased to allow for flexibility in the modeling. In a preferred embodiment, the protein modeler starts with a divergence factor of 0 and increases the divergence factor by 1 Å for each iteration. As the number of iterations increases, the number of violations typically tends to level off. The model generated when the number of violations levels off is typically selected as the three-dimensional structure for the model protein.

Modeling Variable Regions Based on $\psi$ and $\phi$ Angles and Dimers

TABLE 4

| | |
|---|---|
| MURIL4: | -----HGCDKNHLREIIGILNEVTGEGTPCTEMDVPNVLTATKNT |
| HUMIL4: | -EAEAHKCDIT-LQEIIKTLNSLTEQKTLCTELTVTDIFAASKDT |
| TEMPLT: | ------------LQEIIKTLNSLTEQKTLCTELTVTDIFAASKDT |
| MURIL4: | TESELVCRASKVLRIFYLKHGK-TPCLKKNS-------SVLMELQ |
| HUMIL4: | TEKETFCRAATVLRQFYSHHEKDTRCLGATAQQFHRHKQLIRFLK |
| TEMPLT: | TEKETFCRAATVLRQFYSHHEK---CL------------LIRFLK |
| MURIL4: | RLFRAFRCLDSSISCTMNESKSTSLKDFLESLKSIMQMDYS---- |
| HUMIL4: | RLDRNLWGLAGLNSCPVKEADQSTLENFLERLKTIMREKYSKCSS |
| TEMPLT: | RLDRNLWGLAGLNSCPVKEADQSTLENFLERLKTIMREKYSKCSS |

In an alternate embodiment, the present invention provides a method and system for modeling a model protein that bears weak sequence identity to a template protein with a known three-dimensional structure. Proteins with weak sequence identity, but with similar three-dimensional structure, are known as divergent proteins. In this embodiment, the template protein and the model protein are preferably divergent proteins. The positions of the backbone atoms of the structurally conserved regions of the model protein are allowed to deviate from the position of the topologically equivalent atoms in the template protein. The In another embodiment, the present invention provides a method and system for modeling the variable regions of a model protein using the $\psi$ and $\phi$ angles between amino acid pairs of a template protein or a family of template proteins. A variable region modeler generates a collection of $\psi$ and $\phi$ angle values for each amino acid pair in a family of proteins. The variable region modeler creates a matrix of amino acid pairs, such that, each entry in the matrix is a list of all $\psi$ and $\phi$ angle values that are in the variable regions of the family. The variable region modeler models the variable region by randomly selecting a $\psi$ and $\phi$ angle value from the matrix for each amino acid pair in the variable region and calculating the corresponding atomic position information (e.g., Cartesian coordinates).

Each variable region is bounded by a beginning structurally conserved region and an ending structurally conserved region. The variable region modeler generates the atomic position information for the amino acids in the beginning structurally conserved region from the ψ and φ angle values in the corresponding structurally conserved region of a template protein. The variable region modeler then generates atomic position information for the amino acids in the variable region. The variable region modeler successively selects each pair of amino acids in the variable region. For each pair of amino acids, the variable region modeler selects, preferably randomly, an ψ and φ angle value from the corresponding cell in the matrix. The variable region modeler then calculates the atomic positions of the amino acids using the selected ψ and φ angle values. After processing the variable region, the variable region modeler generates the atomic positions for the amino acids in the ending structurally conserved region using the ψ and φ angle values of the corresponding structurally conserved region in the template protein. Finally, the variable region modeler calculates the root mean square (rms) deviation between the ending structurally conserved region of the model protein and the template protein. The rms deviation indicates the degree to which the model for the variable region is consistent with the bounding structurally conserved regions.

In a preferred embodiment, the variable region modeler iteratively generates models and rms deviations for a variable region. The variable region modeler selects the variable region model with smallest rms deviation. As the number of iterations is increased, the likelihood of generating successively smaller rms deviations also increases. In the preferred embodiment, the selection of ψ and φ angle values is random, that is, a Monte Carlo method. Alternatively, other selection criterion can be used. For example, selection of the ψ and φ angle values for each pair on the amino acids that follow and proceed the pair in the model protein. Also, as discussed above, amino acid angle matrix is preferably generated from the variable regions in a family of proteins. Alternately, the matrix can be generated from proteins not in the same family. Also, a matrix can be generated for each corresponding variable region in a family of protein. Each matrix contains the ψ and φ angle values for the corresponding variable region in each protein in the family. One skilled in the art would appreciate that other techniques for generating the matrix may be used.

After the atomic positions for the variable regions in a model protein are generated, then the positions may be used by the protein modeler as constraints to improve the modeling process as described above.

Figures 7, 8:
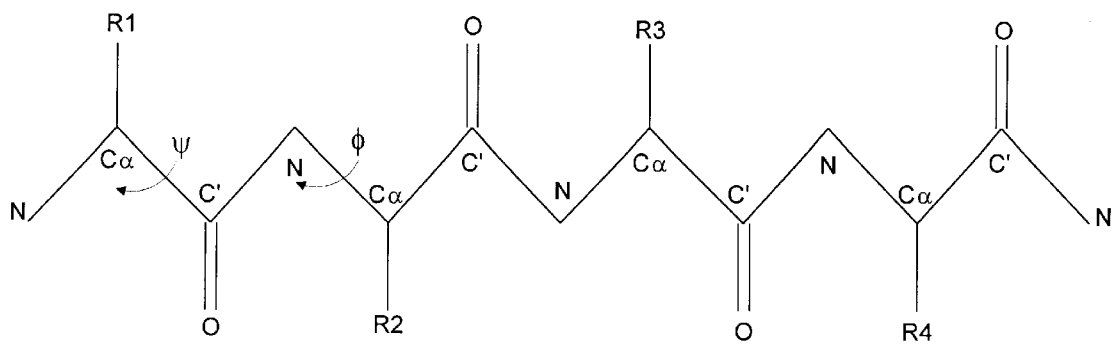
FIG. 7 is a diagram illustrating the $\psi$ and $\phi$ angles between pairs of amino acids.
FIG. 8 is a diagram illustrating the amino acid angle matrix.

FIG. 7 is a diagram illustrating the ψ and φ angles between pairs of amino acids. The peptide bond is planar, that is, the backbone atoms in a peptide bond lie in the same plane. The ψ and φ angles measure the inter-amino acid rotation between the C-alpha and C atoms and the N and C-alpha atoms, respectively. These angles specify the three-dimensional structure of the protein.

FIG. 8 is a diagram illustrating the amino acid angle matrix. The rows and columns of the matrix 801 correspond to each of the 20 standard amino acid. Each entry of the matrix is a list of ψ and φ angle values for the corresponding amino acid pairs. For example, the entry 802 contains the angle values for the amino acid pair asparagine followed by arginine.

Figure 9:
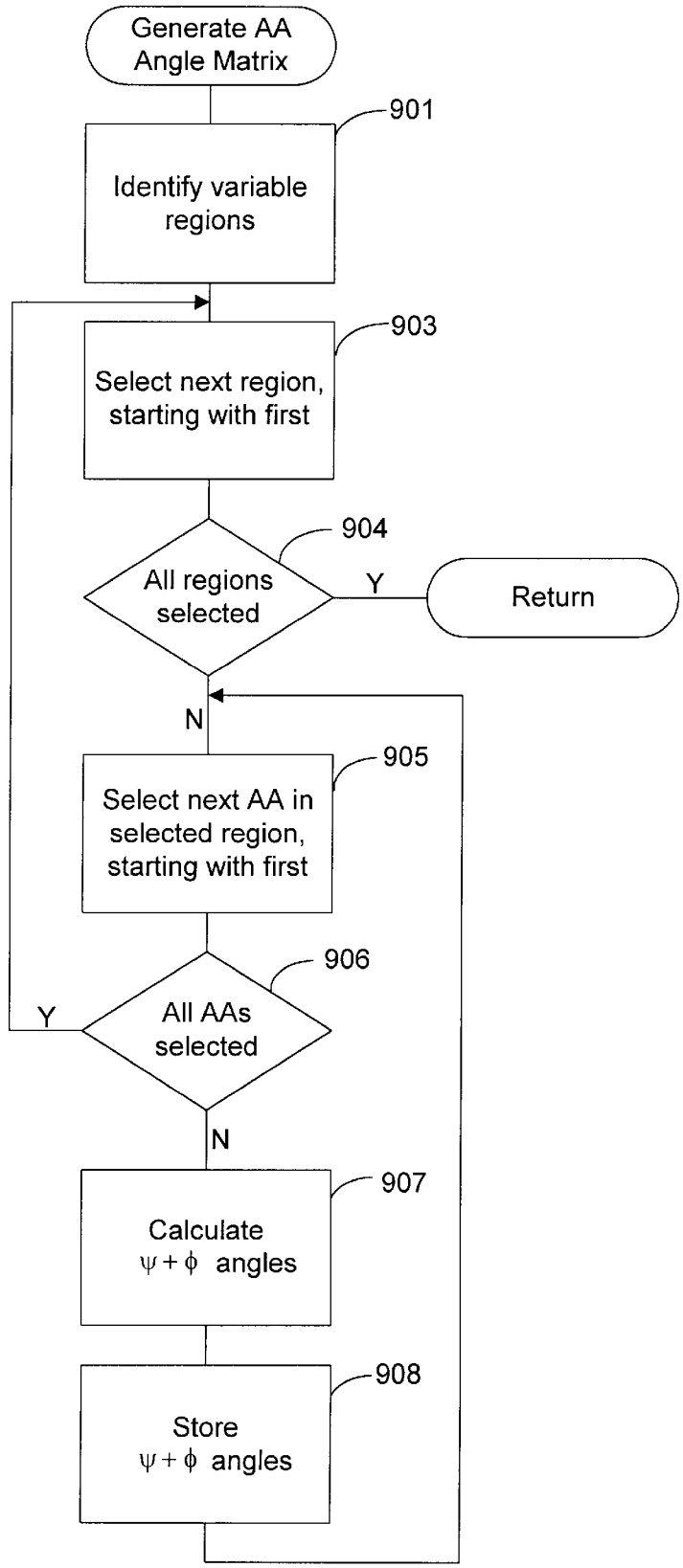
FIG. 9 is a flow diagram of a function that generates the amino acid angle matrix.

FIG. 9 is a flow diagram of a function that generates the amino acid angle matrix. The function inputs the three-dimensional structure of a template protein and updates the matrix based on the ψ and φ angles of the amino acids in the variable regions of the template protein. In step 901, the function identifies the variable regions in the template protein. All regions that are not secondary structural regions (which are identified in the PDB) are variable regions. In step 903 through 908, the function loops processing each variable region and within each variable region each pair of amino acids. In step 903, the function selects the next variable region in the template protein, starting with the first variable region. In step 904, if all the variable regions have already been selected, then the function is complete, else the function continues at step 905. In step 905, the function selects the next amino acid pair in the selected variable region, starting with the first. In step 906, if all the amino acid pairs in the selected variable region have already been selected, then the function loops to step 903 to select the next variable region, else the function continues at step 907. In step 907, the function calculates the ψ and φ angles based on the position information of the selected amino acids. In step 908, the function adds the calculated ψ and φ angle values to the list of angles in the matrix at the entry corresponding to the pair of the selected amino acids. The function then loops to step 905 to select the next pair of amino acids.

Figure 10:
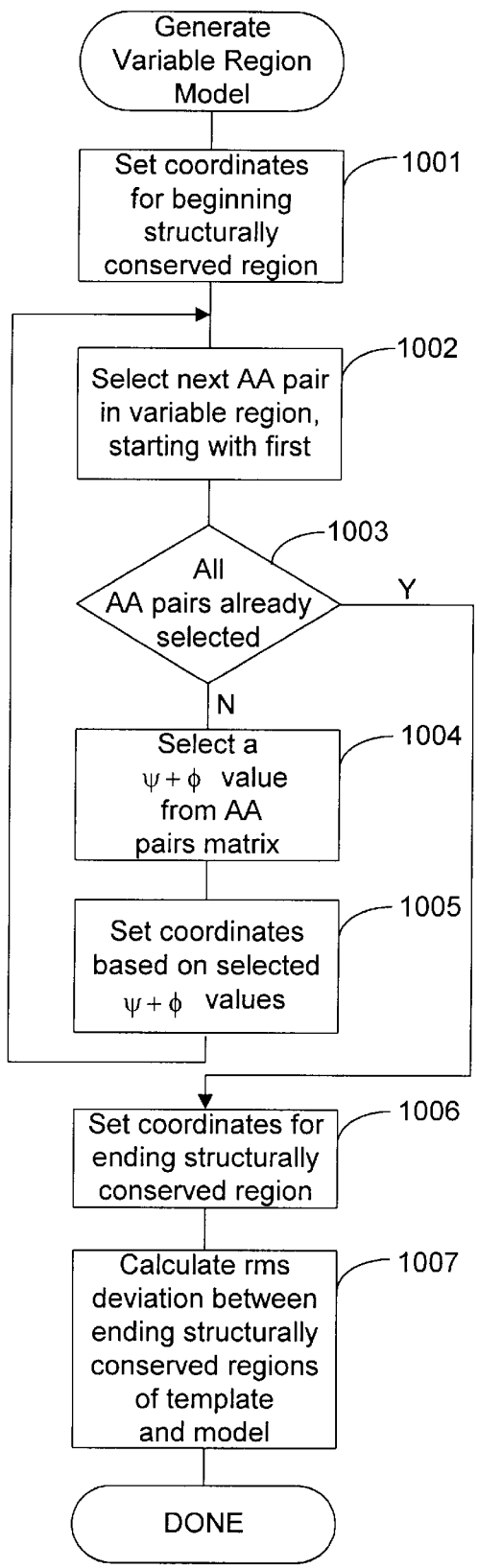
FIG. 10 is a flow diagram of a function to generate a variable region model for a model protein based on the amino acid angle matrix.

FIG. 10 is a flow diagram of a function to generate a variable region model for a model protein based on the amino acid angle matrix. The function outputs an rms deviation value for the generated model. In a preferred embodiment, this function is invoked multiple times, and the model with the smallest rms deviation is selected as the model for the variable region. In step 1001, the function sets the position information for the beginning structurally conserved region. The position information is generated from the ψ and φ angle values of the corresponding structurally conserved region in the template protein. Alternatively, the coordinates can be obtained directly from the three-dimensional structure of the template protein. In steps 1002 through 1005, the function loops selecting each pair of amino acids in the variable region, selecting ψ and φ angle values, and setting position information for the atoms of the selected amino acids. In step 1002, the function selects the next amino acid pair in the variable region, starting with the first. In step 1003, if all the amino acid pairs in the variable region have been selected, then the function continues at step 1006 to process the ending structurally conserved region, else the function continues at step 1004. In step 1004, the function selects an ψ and an φ angle value from the matrix at the entry corresponding to the selected amino acid pair.

In a preferred embodiment, the ψ and φ angles are selected randomly from the list. Alternatively, the ψ and φ angles can be selected based on the probability of occurrence of the angles in the template protein or family of template proteins. Also the ψ and φ angle values can be selected based on a probability that certain ψ and φ angle values proceed or follow other ψ and φ angle values. In step 1005, the function calculates position information for each backbone atom in the selected pair of amino acids based on the angles and the calculated position information of the adjacent amino acid. The function also calculates the position information for the side chain atoms and loops to step 1002 to select the next pair of amino acids. In step 1006, the fulnction determines the position information for the amino acids in the ending structurally conserved regions. The position information is calculated based on the calculated position of the last amino acid in the variable region and the ψ and φ angles for each pair of amino acids in the ending structurally conserved region of the template protein. In step 1007, the function calculates the rms deviation between the ending structurally conserved region of the model protein and the corresponding region in the template protein.

In alternate embodiment, the three-dimensional structure of a protein can be modeled de novo from the collected ψ and φ angle values. A matrix of ψ and φ angle values can be generated for all proteins in the PDB or for a family of proteins. The positional information can then be generated for each pair of amino acids in the model protein by selecting (e.g. randomly) ψ and φ angle values from the matrix. The compactness of the resulting three-dimensional structure can then be computed. The compactness can include a measurement of the volume of the three-dimensional structure, a measurement of the maximum inter-atomic distance, or a measurement of the density. The three-dimensional structure that is most compact can then be selected as the foled form of the made protein. Also, the ψ and φ angle values can be combined with other constraints as described above to model a protein.

Modeling Variable Regions Based on ψ and φ Angles and Tetramers

In another embodiment, the present invention provides a method and system for modeling the variable regions of a model protein using the ψ and φ angles between amino acid pairs and a classification of the amino acids that are upstream and downstream from the amino acid pair. An amino acid is considered to be upstream from an amino acid pair if it is to the left of the pair in a sequence listing and downstream if it is to the right of the pair in a sequence listing. For example, in the sequence listing "HGCDKN," the amino acids H and G are upstream from the amino acid pair "CD," and the amino acids K and N are downstream from that pair. An amino acid pair and its adjacent upstream and downstream amino acids form a tetramer. For example, the amino acid pair "CD" is part of the tetramer "GCDK."

The variable region modeler generates a collection of ψ and φ angle values for each amino acid pair in a family of proteins. The variable region modeler creates an array of amino acid pairs (i.e., a 20-by-20 matrix). Each entry in the matrix is a sub-matrix of classifications of the upstream and downstream amino acids that are adjacent to the amino acid pair. Each entry in the sub-matrix is a list of all the ψ and φ angle values that are in the variable regions of the family of proteins for that amino acid pair with the corresponding classifications of adjacent amino acids in the tetramer. Since the matrix and sub-matrix can be considered to be a four-dimensional array indexed by the amino acids of the tetramer, the matrix is referred to as a tetramer matrix. The variable region modeler models the variable region by randomly selecting ψ and φ angle values from the tetramer matrix for each amino acid pair in the variable region and calculates the corresponding atomic position information in the same manner, as used for modeling the variable region using dimers, as discussed above.

In one embodiment, each type of adjacent amino acid is simply classified as its own classification, that is, the sub-matrix would also be a 20-by-20 matrix. Thus, each possible tetramer would have its own list of ψ and φ angle values. However, since there are 160,000 ($20^4$) possible tetramers, the number of ψ and φ angle values for some tetramers may be small or empty. Such a small sample of ψ and φ angle values may not be sufficient to represent a statistically adequate sample. Consequently, in a preferred embodiment, the adjacent amino acids that are upstream and downstream from an amino acid pair are classified as hydrophobic (A,V,F,I,L,P,M,G); charged (D,E,K,R); or polar (S,T,Y,H,C, N,Q,W) amino acids. Using these three classifications, the sub-matrix is a 9-by-9 matrix and thus these are only 3600 ($20^2 \times 3^2$) possible tetramer classifications. Referring to the example above, the adjacent amino acid G that is upstream from the amino acid pair "CD" is classified as hydrophobic, and the adjacent amino acid K that is downstream is charged. Thus, the classified tetramer is hydrophobic-C-D-charged. Other classifications of amino acids would be acceptable, for example the amino acids G and P could form a separate classification for structural regions. Also, as the PDB grows more classification may be feasible.

In an alternate embodiment, the variable region modeler customizes the tetramer matrix to the variable region to be modeled. The variable region modeler identifies conformational preferences within the variable region using the tetramer matrix. The variable region modeler then creates a new tetramer matrix containing those ψ and φ angle values that would contribute to a three-dimensional structure that is consistent with the conformational preference. The variable region modeler customizes the tetramer matrix by first determining a putative conformation for each overlapping hexamer in the variable region. The possible conformations are preferably helical, extended, and turns. The variable region modeler uses the ψ and φ angle values of the tetramer matrix to generate a large number of possible three-dimensional structures for each hexamer. The variable region modeler then determines the conformations of these threedimensional structures. Based on this determination, the variable region modeler selects a putative conformation for the hexamer. Once the putative conformation is selected for the hexamer, the variable region modeler takes each of the ψ and φ angle values that were used to generate a three-dimensional hexamer structure that has the same conformation as the putative conformation and adds those values to a filtered tetramer matrix. Thus, the filter tetramer matrix has ψ and φ angle values that contributed to the three-dimensional hexamer structure with the same conformation as the putative conformation. The variable region modeler then generates a model of the variable region in a manner that is analogous to the variable region modeler discussed above.

In a preferred embodiment, the variable region modeler uses hexamers when identifying the conformation of portions of the variable regions of the model protein. The length of the amino acid used to identify conformations should be small enough to reflect only local interactions and large enough to contain all the local interactions. Ideally, the length would vary based on characteristics of the model protein. However, a length of six or seven is preferred because a length of five does not appear to be long enough to represent a conformation, whereas a length of eight is more than long enough to represent a conformation.

Figure 11:
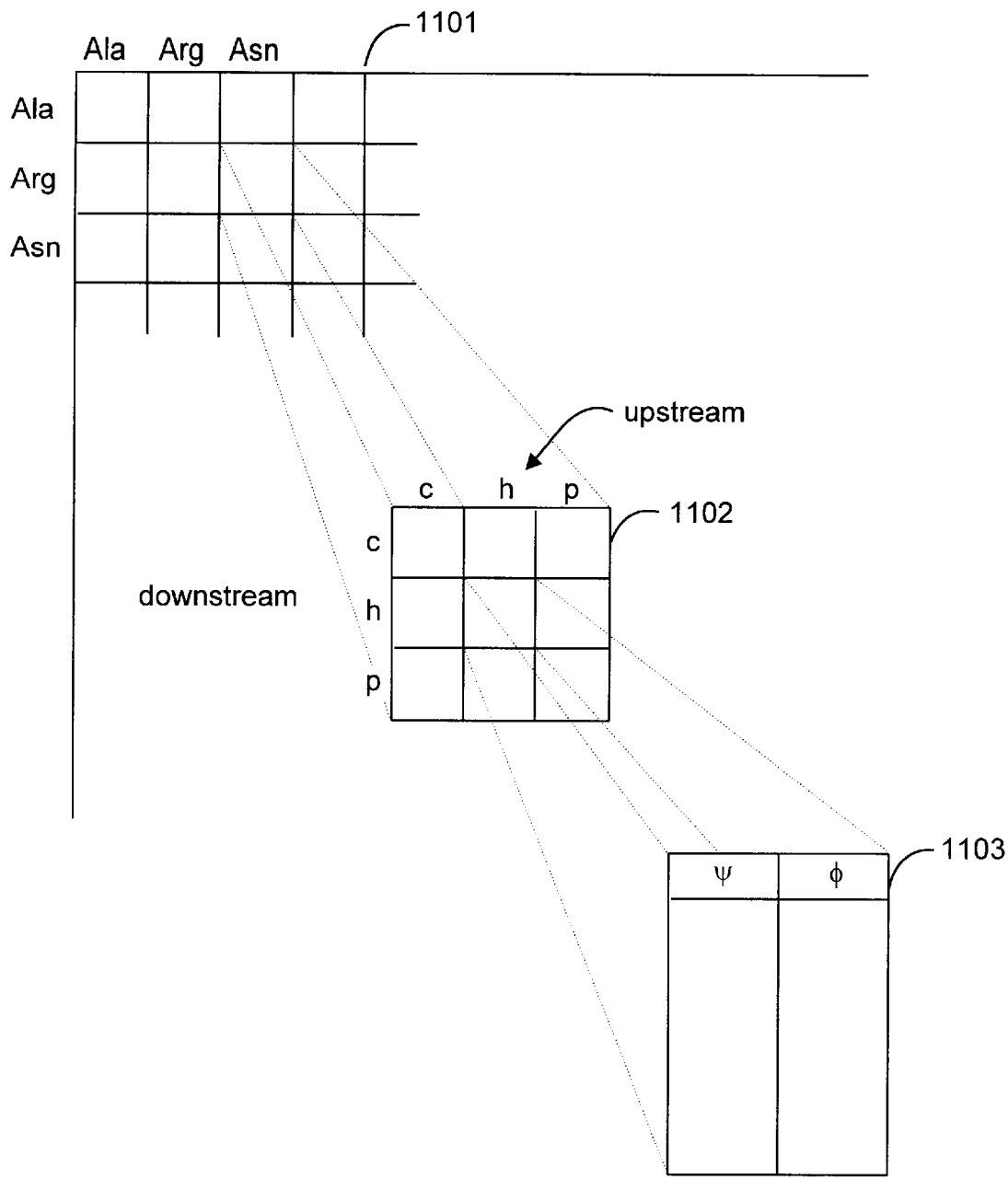
FIG. 11 is a diagram illustrating the tetramer matrix.

FIG. 11 is a diagram illustrating the tetramer matrix. The tetramer matrix can be considered to be a multi-dimensional array indexed by the amino acids in the amino acid pair and the classifications of the adjacent upstream and downstream amino acid. Tetramer matrix 1101 is a square matrix with each entry corresponding to an amino acid pair. Each entry contains a sub-matrix referred to as a classification matrix 1102. The classification matrix is a square matrix whose rows and columns correspond to the amino acid classifications charged (C), hydrophobic (H), and polar (P). Thus, the classification matrix has nine entries. Each entry of the classification matrix is a list of ψ and φ angle values for the corresponding classified tetramer. For example, the entry 1103 contains the angle values for the classified tetramer with a hydrophobic amino acid, asparagine, arginine, and another hydrophobic amino acid. Thus, the adjacent upstream and downstream amino acids are both classified as hydrophobic.

Figure 12:
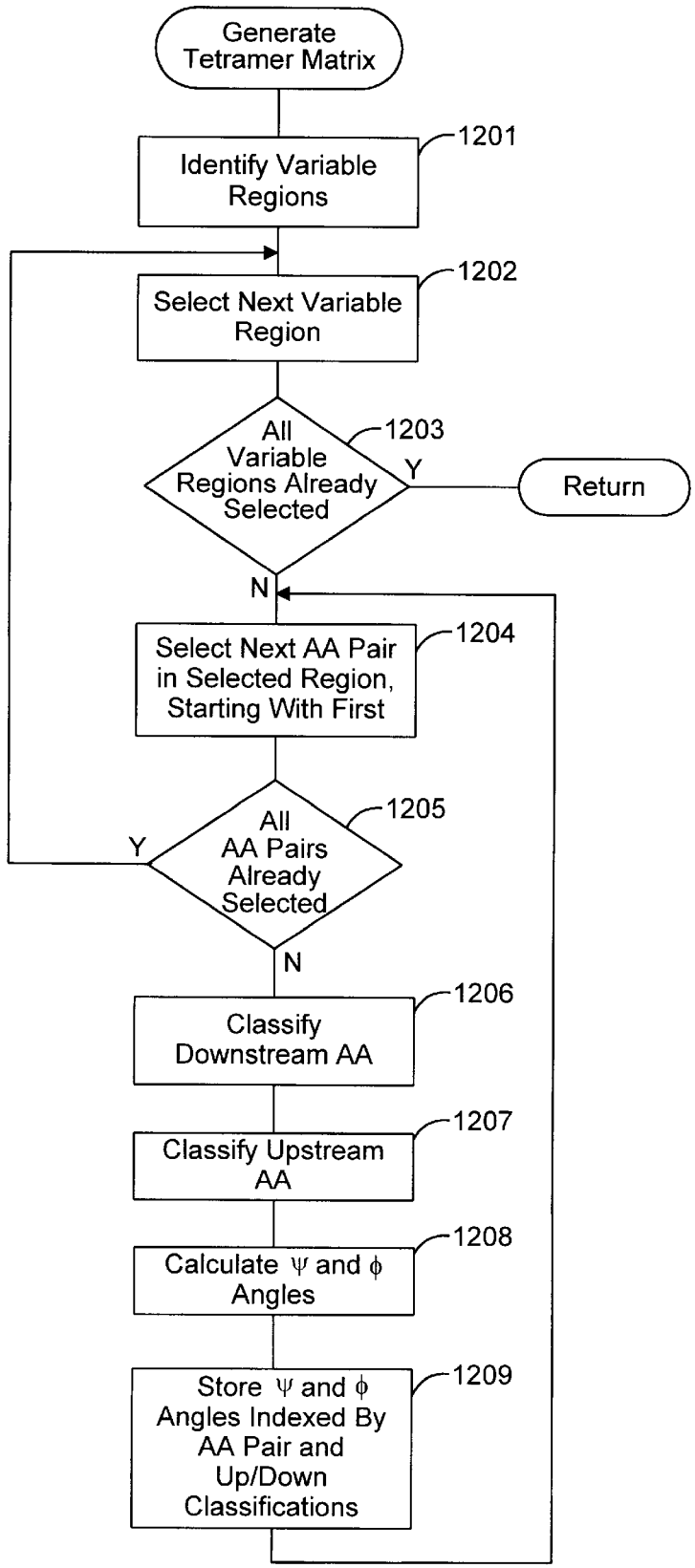
FIG. 12 is a flow diagram of the procedure to generate a tetramer matrix.

FIG. 12 is a flow diagram of a function to generate a tetramer matrix. The function inputs the three-dimensional structure of a protein and updates the tetramner matrix based on the ψ and φ angles of the dimers in each overlapping tetramer in variable regions. The variable region modeler invokes this function for each protein in the family of proteins to generate a representative collection of ψ and φ angle values. In step 1201, the function identifies the variable regions in the protein. In steps 1202–1209, the function loops processing each variable region and within each variable region each pair of amino acids. In step 1202, the function selects the next variable region of the protein starting with the first variable region. In step 1203, if all the variable regions have already been selected, then the function completes, else the function continues at step 1204. In steps 1204–1209, the function loops processing each amino acid pair in the selected variable region. In step 1204, the function selects the next amino acid pair in the selected variable region, starting with the first. In step 1205, if all the amino acid pairs in the selected variable region have already been selected, then the function loops to step 1202 to select the next variable region, else the function continues at step 1206. In step 1206, the function classifies the adjacent amino acid that is downstream to the selected pair. In step 1207, the function classifies the adjacent amino acid that is upstream to the selected amino acid pair. In step 1208, the function selects the ψ and φ angles for the selected amino acid pair. In step 1209, the function stores the ψ and φ angles into the tetramer matrix indexed by the selected amino acid pair and the classifications for the adjacent downstream and upstream amino acids and loops to step 1204 to select the next amino acid pair in the selected variable region.

Figure 13:
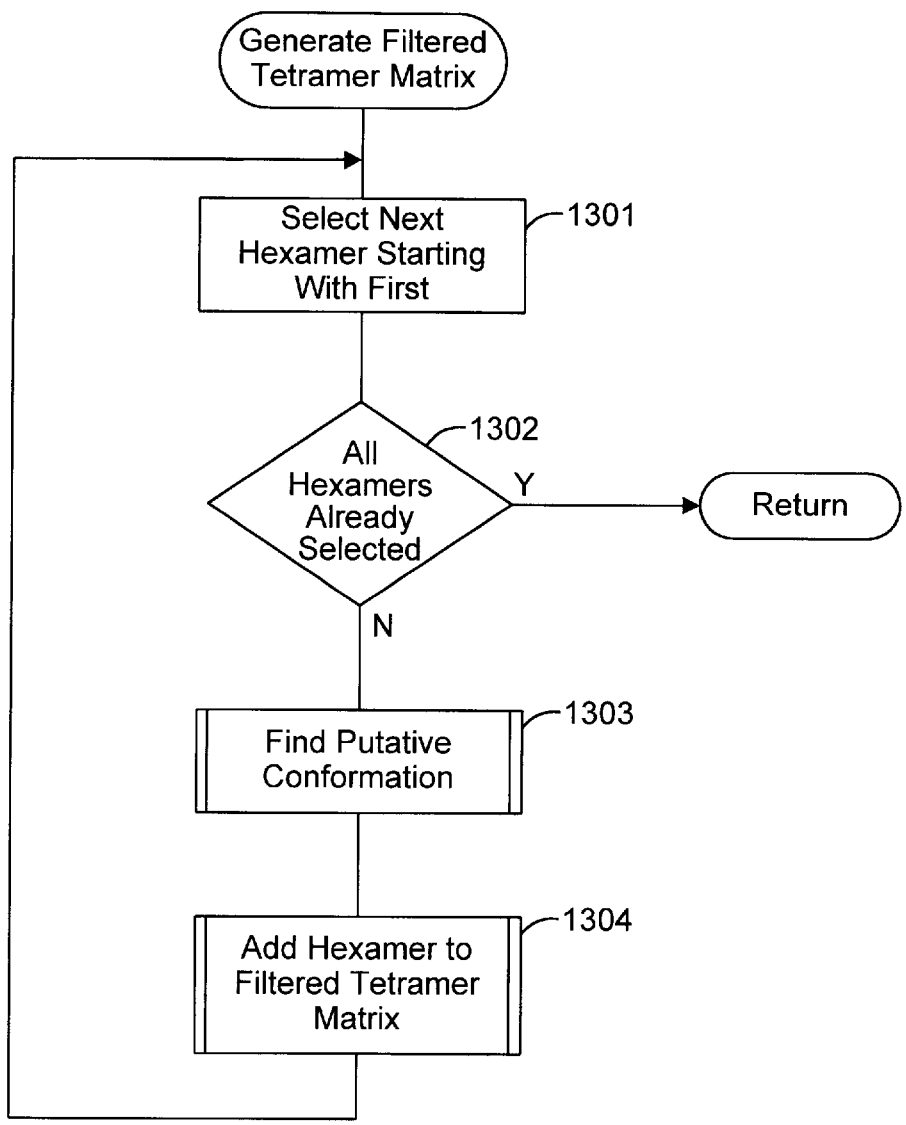
FIG. 13 is a flow diagram for the procedure to generate a filtered tetramer matrix.

FIG. 13 is a flow diagram for a procedure to generate a filtered tetramer matrix. This function inputs the tetramer matrix and the variable region to be modeled and generates a filtered tetramer matrix. The function processes overlapping pairs of hexamers in the variable region of the protein to be modeled and generates the filtered tetramer matrix. In steps 1301–1304, the function loops selecting each hexamer starting with the first. In step 1302, if all the hexamers have already been selected, then the function returns, else the function continues at step 1303. In step 1303, the function invokes a function to find a putative conformation for the selected hexamer. In step 1304, the function adds the ψ and φ angle values corresponding to the three-dimensional structure of the selected hexamer that match the putative conformation to the filtered tetramer matrix and loops to step 1301 to select the next hexamer in the variable region of the protein to be modeled.

Figure 14:
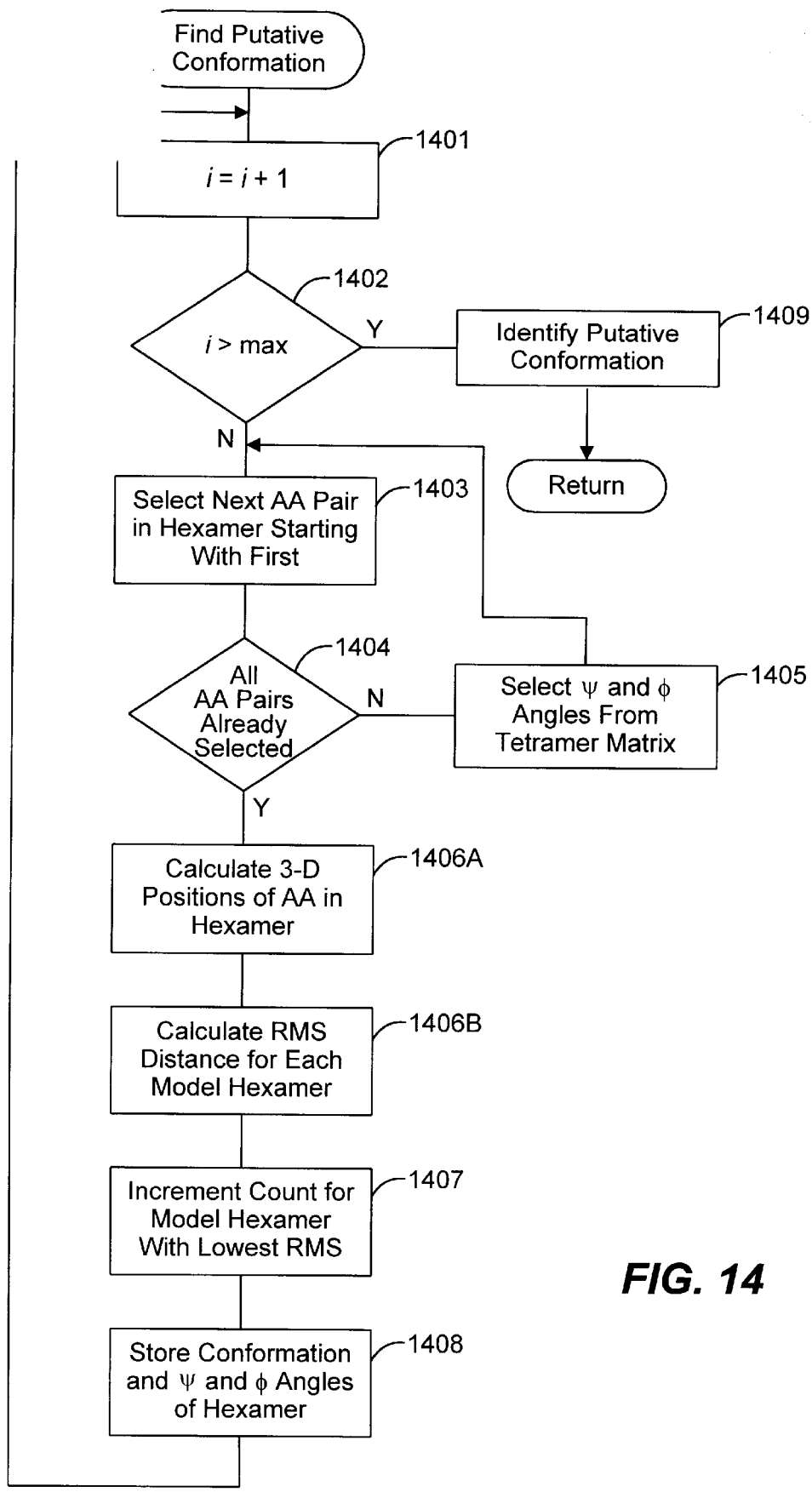
FIG. 14 is a flow diagram of the function to find a putative conformation for a hexamer.

FIG. 14 is a flow diagram of a function to find a putative conformation for a hexamer. The function inputs the tetramer matrix and a hexamer. The function models the three-dimensional structure of the hexamer based on ψ and φ angle values that are randomly selected from the tetramer matrix. In a preferred embodiment, the function generates 10,000 three-dimensional structures for the hexamer. The function then determines, for each three-dimensional structure, whether the structure most closely conforms to a helical, extended, or turns model hexamer. The function returns as the putative conformation the model hexamer to which most of the hexamer structures conform. In steps 1401–1408, the function loops determining the three-dimensional structure of the hexamer based on randomly selected ψ and φ angle values from the tetramer matrix. In step 1401, the function increments the count of the three-dimensional structures for the hexamer that have been generated. In step 1402, if the count of three-dimensional structures for the hexamer exceeds a maximum amount, then the function continues at step 1409, else the function continues at step 1403. In steps 1403–1405, the function loops selecting each amino acid pair in the hexamer and assigning ψ and φ angle values randomly selected from the tetramer matrix. In step 1403, the function selects the next amino acid pair in the hexamer starting with the first classifies the adjacent downstream and upstream amino acids. In step 1404, if all the amino acid pairs in the hexamer have already been selected, then the function continues at step 1406A, else the function continues at step 1405. In step 1405, the function randomly selects ψ and φ angle values from the tetramer matrix, assigns the angle values to the selected amino acid pair, loops to step 1403 to select the next amino acid pair in the hexamer. In step 1406A, the function calculates the three-dimensional positions of the amino acids in the hexamer based on the assigned ψ and φ angle values. In step 1406, the function calculates the root mean square (RMS) deviation of the calculated three-dimensional structure of the hexamer from each of the three model hexamers. In step 1404, the function increments the count of the model hexamer with lowest RMS deviation from the three-dimensional structure. That is, the function determines the conformation of the generated three-dimensional hexamer structure. In step 1408, the function stores the assigned ψ and φ angle values for the hexamer along with an indication of the determined conformation and loops to step 1401. In step 1409, the function identifies the model hexamer with the highest count as the putative conformation and returns.

Figure 15:
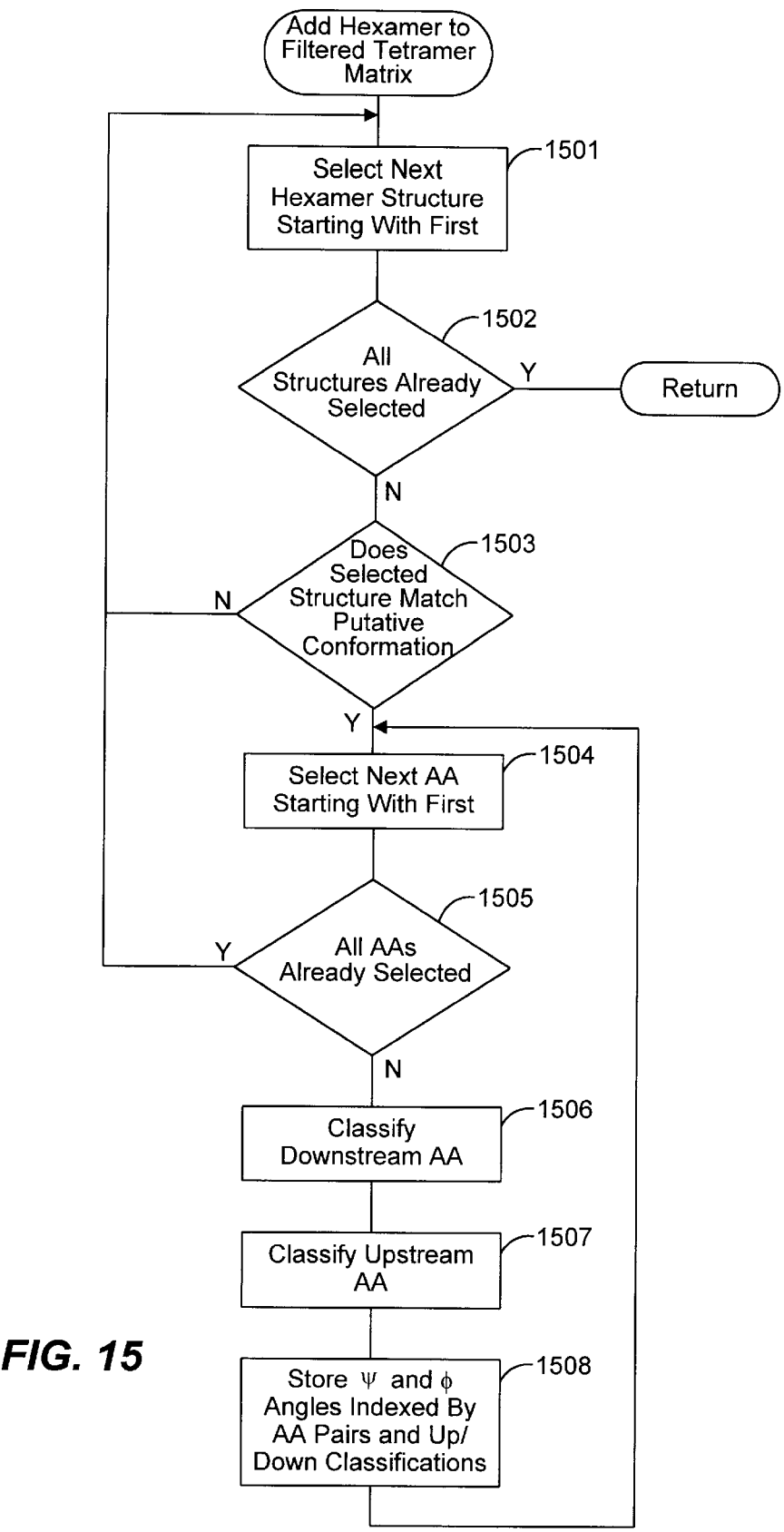
FIG. 15 is a flow diagram of a function to add information for a hexamer to the filtered tetramer matrix.

FIG. 15 is a flow diagram of a function to add information for a hexamer to the filtered tetramer matrix. This function adds the ψ and φ angles values to the filtered tetramer matrix for each three-dimensional hexamer structure with a conformation that matches the putative conformation. In step 1501, the function selects the next three-dimensional hexamer structure starting with the first. In step 1502, if all the hexamer structures have already been selected, then the function returns, else the function continues at step 1503. In step 1503, if the conformation of the selected hexamer structure matches the putative conformation, then the function continues at step 1504, else the function loops to step 1501 to select the next hexamer structure. In step 1504, the function selects the next amino acid pair in the selected hexamer starting with the first. In step 1505, if all the amino acid pairs in the selected hexamer have already been selected, then the procedure loops to step 1501 to select the next hexamer structure. In step 1506, the function classifies the adjacent amino acid that is downstream from the selected amino acid pair. In step 1507, the function classifies the adjacent amino acid that is upstream from the selected amino acid pair. Alternatively, the classification of adjacent amino acids can be done once for each invocation of this function or passed to this function. In step 1508, the function stores the ψ and φ angle values of the selected amino acid pair indexed by the selected amino acid pair and the downstream and upstream classifications into the filtered tetramer matrix and loops to step 1504 to select the next amino acid pair in the selected hexamer.

Figure 16:
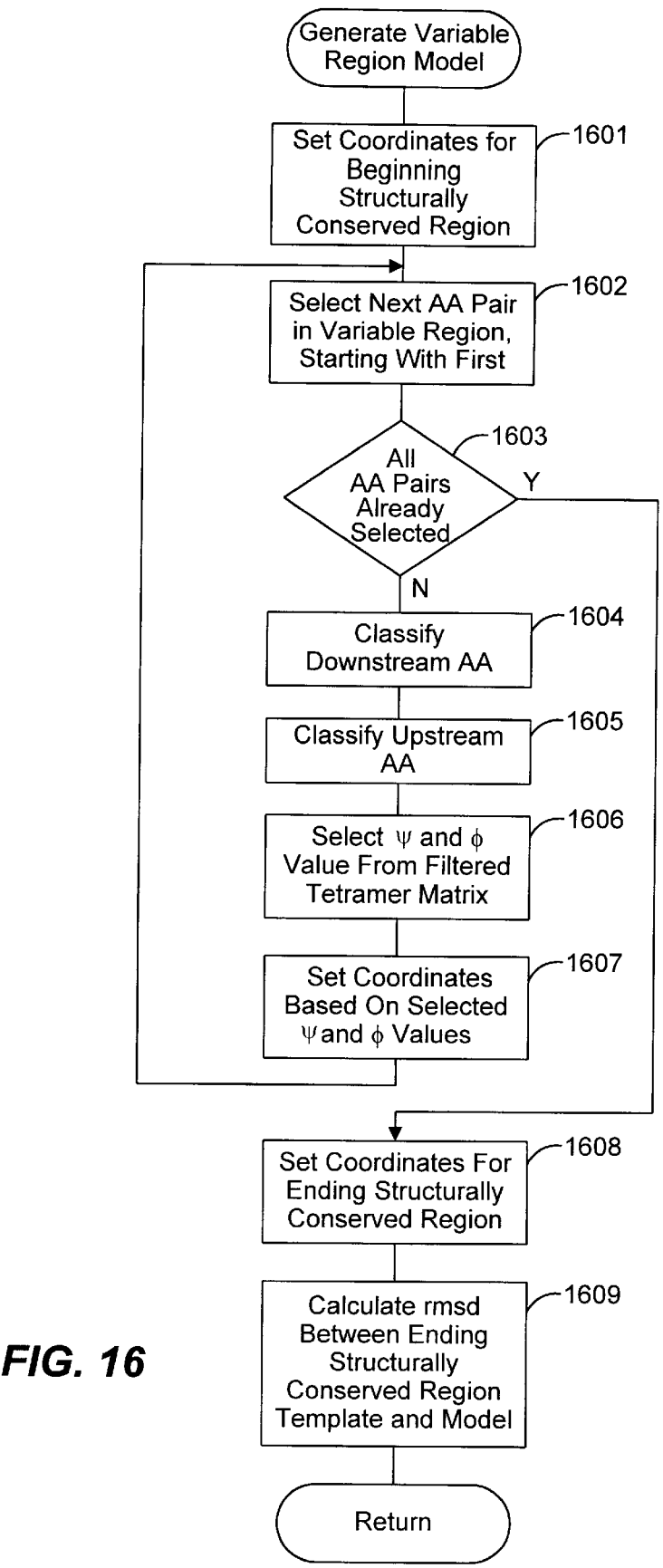
FIG. 16 is a flow diagram of a procedure to generate the variable region model.

FIG. 16 is a flow diagram of a function to generate the variable region model. The function inputs the sequence of the model protein and the three-dimensional structure of a template protein. The function models the three-dimensional structure of the model protein using the filtered tetramer matrix. The function calculates and returns the RMS deviation value between the generated model and the template protein. In a preferred embodiment, this function is invoked multiple times, and the model with the smallest RMS deviation is selected as the model for the variable region. In step 1601, the function sets the position information for the beginning structurally conserved region of the model protein. The position information is generated from the ψ and φ angle values of the corresponding structurally conserved region of the template protein. Alternatively, the coordinates can be obtained directly from the three-dimensional structure of the template protein. In steps 1602–1605, the function loops selecting each pair of amino acids in the variable region, selecting ψ and φ angle values, and setting the position information for the atoms of selected amino acids. In step 1602, the function selects the next amino acid pair in the variable region, starting with the first. In step 1603, if all the amino acid pairs in the variable region have been selected, then the function continues at step 1608 to process the ending structurally conserved region, else the function continues at step 1604. In step 1604, the function classifies the adjacent amino acid that is downstream to the selected amino acid pair. In step 1605, the function classifies the adjacent amino acid that is upstream to the selected amino acid pair. In step 1606, the function randomly selects a ψ and φ angle values from the filtered tetramer matrix based on the classified tetramer. Alternatively, the original unfiltered tetramer matrix or tetramer matrix with other classifications of downstream and upstream amino acids can be used. In step 1607, the function calculates the position information for each backbone atom in the selected pair of amino acids based on angles and the calculated position information of the adjacent amino acid that is downstream. The function also calculates the position information for the side chain atoms and loops to step 1602 to select the next amino acid pair. In step 1608, the function determines the position information for the amino acids in the ending structurally conserved region. The position information is calculated based on the calculated position of the last amino acid in the variable region and the ψ and φ angles for each pair of amino acids in the ending structurally conserved region of the template protein. In step 1609, the function calculates the RMS deviation between the ending structure conserved region of the model protein and the corresponding region of the template protein and returns.

Although the present invention has been described in terms of a preferred embodiment, it is not intended that the invention be limited to this embodiment. Modifications within the spirit of the invention will be apparent to those skilled in the art, the scope of the present invention is defined by the claims which follow.

---

We claim:

1. A method in a computer system for generating a collection of relative positional information between pairs of amino acids for use in modeling a three-dimensional structure of a variable region of a model protein, the computer system having relative positional information between pairs of amino acids in the variable regions of a collection of proteins, the method comprising:
   for each protein in the collection of proteins,
      for each pair of amino acids in the variable regions of the protein, in the collection of proteins,
         classifying the amino acids that are downstream and upstream from the amino acid pair; and
         storing the relative positional information for the amino acid pair based on the amino acids in the amino acid pair and on the classification of the amino acids that are downstream and upstream so that the position of each amino acid in the variable region of the model protein can be modeled based on the stored relative positional information in the collection of proteins and based on classification of amino acids that are down stream and up stream from pairs of amino acids in the model protein.

2. The method of claim 1 wherein the relative positional information includes $\psi$ and $\phi$ angle values between pairs of amino acids.

3. The method of claim 1 wherein the amino acids are classified according to the amino acids that are adjacent to the amino acid pair.

4. The method of claim 3 wherein the adjacent amino acids are classified as charged, hydrophobic, and polar.

5. A method in a computer system for modeling a three-dimensional structure of a variable region of a model protein, the model protein having amino acids, the amino acids having positions within a three-dimensional structure, the method comprising the steps of:

generating a collection of relative positional information between pairs of amino acids, the relative position information being classified by a tetramer of amino acids that include the amino acid pair;

establishing a positional for a first amino acid of the variable region; and for each amino acid pair in the variable region, generating a model position for the amino acids based on a classification of the tetramer that includes the amino acid and based on the collection of relative positional information for the pairs of amino acids.

6. The method of claim 5 including the step of, for each combination of pairs of amino acids in variable regions of a family of proteins, collecting the $\psi$ and $\phi$ angle values for the pair of amino acids and wherein the step of generating a model position bases the model position on one of the collected $\psi$ and $\phi$ angle values.

7. The method of claim 6 wherein the step of generating a model position bases the model position on a randomly selected one of the collected $\psi$ and $\phi$ angle values.

8. The method of claim 5 including the step of generating a model position for the amino acids of the adjacent structurally conserved regions based on relative position information between pairs of amino acids.

9. The method of claim 8 wherein the step of generating a model position for the amino acids of the adjacent structurally conserved region is based on the $\psi$ and $\phi$ angle values in a corresponding region of a template protein.

10. The method of claim 8 including the step of comparing the generated model position for the amino acids of the adjacent structurally conserved region to positions in a corresponding region in a template protein to indicate effectiveness of the modeling.

11. A method in a computer system for modeling a three-dimensional structure of a variable region of a model protein, the model protein having amino acids, the method comprising the step of establishing positional information for the amino acids in the variable region based on $\psi$ and $\phi$ angle values between pairs of amino acids in a collection of proteins such that the pairs of amino acids are classified according to their downstream and upstream amino acids.

12. The method of claim 11 wherein the model protein has a structurally conserved region that is adjacent to the variable region, and including the steps of:

establishing positional information for the amino acids in the adjacent structurally conserved region based on the established positional information of the amino acids in the variable region and based on $\psi$ and $\phi$ angle values in a corresponding structurally conserved region of the template protein; and comparing the established positional information of the amino acids of the adjacent structurally conserved region to positional information of the corresponding structurally conserved region of the template protein to measure the effectiveness of the modeling.

13. The method of claim 11 including the step of collecting $\psi$ and $\phi$ angle values for pairs of amino acids in a template protein and classifying the collected $\psi$ and $\phi$ values based on the adjacent downstream and upstream amino acids and wherein the step of establishing bases the positional information on the collected $\psi$ and $\phi$ angle values.

14. The method of claim 13 wherein the step of establishing includes the step of randomly selecting a collected $\psi$ and $\phi$ angle value.

15. The method of claim 13 wherein the step of collecting collects $\psi$ and $\phi$ angle values for pairs of amino acids in a family of template proteins.

16. A method in a computer system for modeling a three-dimensional structure for a variable region of a model protein, the protein having amino acids, the variable region having a corresponding beginning structurally conserved region and a corresponding ending structurally conserved region, the method comprising the steps of:

collecting $\psi$ and $\phi$ angle values for pairs of amino acids in a family of template proteins and classifying each $\psi$ and $\phi$ angle value according to the amino acids in the pair and an amino acid that is adjacent to the pair;

generating three-dimensional positional information for the amino acids in the beginning structurally conserved region;

generating three-dimensional positional information for the amino acids in the variable region based on the collected $\psi$ and $\phi$ angle values and based on the generated positional information for the beginning structurally conserved region;

generating three-dimensional positional information for the amino acids in the ending structurally conserved region based on the generated positional information for the variable region and based on positional information for a corresponding ending structurally conserved region in a template protein; and comparing the generated positional information for the amino acids in the ending structurally conserved regions to positional information for the amino acids in the corresponding structurally conserved region in the template protein to indicate correctness of the model.

17. The method of claim 16 including the step of randomly selecting collected $\psi$ and $\phi$ angle values when generating the positional information for the amino acids in the variable region.

18. The method of claim 16 including the step of repeating the steps of generating and comparing, and including the step of selecting, as the model of the variable region, generated positional information for the amino acids in the variable region when the generated positional information of the amino acids in the ending structurally conserved region most closely compares to positional information in the corresponding structurally conserved region in the template protein.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 118 amino acids
        ( B ) TYPE: amino acid
        ( C ) STRANDEDNESS: single
        ( D ) TOPOLOGY: linear ( x i ) SEQUENCE DESCRIPTION: SEQ ID NO:1:

```
His Gly Cys Asp Lys Asn His Leu Arg Glu Ile Ile Gly Ile Leu Asn
 1               5                  10                      15

Glu Val Thr Gly Glu Gly Thr Pro Cys Thr Glu Met Asp Val Pro Asn
            20                  25                  30

Val Leu Thr Ala Thr Lys Asn Thr Thr Glu Ser Glu Leu Val Cys Arg
            35              40                  45

Ala Ser Lys Val Leu Arg Ile Phe Tyr Leu Lys His Gly Lys Thr Pro
        50              55                  60

Cys Leu Lys Lys Asn Ser Ser Val Leu Met Glu Leu Gln Arg Leu Phe
65              70                  75                      80

Arg Ala Phe Arg Cys Leu Asp Ser Ser Ile Ser Cys Thr Met Asn Glu
            85                      90              95

Ser Lys Ser Thr Ser Leu Lys Asp Phe Leu Glu Ser Leu Lys Ser Ile
            100                 105                 110

Met Gln Met Asp Tyr Ser
            115
```

( 2 ) INFORMATION FOR SEQ ID NO:2:

( i ) SEQUENCE CHARACTERISTICS:
        ( A ) LENGTH: 133 amino acids
        ( B ) TYPE: amino acid (C) STRANDEDNESS: single
(D) TOPOLOGY: linear (xi) SEQUENCE DESCRIPTION: SEQ ID NO:2:

```
Glu Ala Glu Ala His Lys Cys Asp Ile Thr Leu Gln Glu Ile Ile Lys
 1               5                  10                   15
Thr Leu Asn Ser Leu Thr Glu Gln Lys Thr Leu Cys Thr Glu Leu Thr
             20                  25                  30
Val Thr Asp Ile Phe Ala Ala Ser Lys Asp Thr Thr Glu Lys Glu Thr
             35                  40                  45
Phe Cys Arg Ala Ala Thr Val Leu Arg Gln Phe Tyr Ser His His Glu
         50              55                  60
Lys Asp Thr Arg Cys Leu Gly Ala Thr Ala Gln Gln Phe His Arg His
 65                  70                  75                   80
Lys Gln Leu Ile Arg Phe Leu Lys Arg Leu Asp Arg Asn Leu Trp Gly
                 85                  90                  95
Leu Ala Gly Leu Asn Ser Cys Pro Val Lys Glu Ala Asp Gln Ser Thr
             100                 105                 110
Leu Glu Asn Phe Leu Glu Arg Leu Lys Thr Ile Met Arg Glu Lys Tyr
         115                 120                 125
Ser Lys Cys Ser Ser
    130
```

(2) INFORMATION FOR SEQ ID NO:3:

(i) SEQUENCE CHARACTERISTICS:
 (A) LENGTH: 108 amino acids
 (B) TYPE: amino acid
 (C) STRANDEDNESS: single
 (D) TOPOLOGY: linear (xi) SEQUENCE DESCRIPTION: SEQ ID NO:3:

```
Leu Gln Glu Ile Ile Lys Thr Leu Asn Ser Leu Thr Glu Gln Lys Thr
 1               5                  10                   15
Leu Cys Thr Glu Leu Thr Val Thr Asp Ile Phe Ala Ala Ser Lys Asp
             20                  25                  30
Thr Thr Glu Lys Glu Thr Phe Cys Arg Ala Ala Thr Val Leu Arg Gln
         35                  40                  45
Phe Tyr Ser His His Glu Lys Cys Leu Leu Ile Arg Phe Leu Lys Arg
    50                  55                  60
Leu Asp Arg Asn Leu Trp Gly Leu Ala Gly Leu Asn Ser Cys Pro Val
 65                  70                  75                   80
Lys Glu Ala Asp Gln Ser Thr Leu Glu Asn Phe Leu Glu Arg Leu Lys
                 85                  90                  95
Thr Ile Met Arg Glu Lys Tyr Ser Lys Cys Ser Ser
             100                 105
```